(12) United States Patent
Abkai et al.

(10) Patent No.: US 9,672,641 B2
(45) Date of Patent: Jun. 6, 2017

(54) METHOD, APPARATUS, AND COMPUTER READABLE MEDIUM FOR REMOVING UNWANTED OBJECTS FROM A TOMOGRAM

(71) Applicant: Sirona Dental Systems GmbH, Bensheim (DE)

(72) Inventors: Ciamak Abkai, Heddesheim (DE); Kai Lindenberg, Wersau (DE)

(73) Assignee: Sirona Dental Systems GmbH, Bensheim (DE)

( * ) Notice: Subject to any disclaimer, the term of this patent is extended or adjusted under 35 U.S.C. 154(b) by 128 days.

(21) Appl. No.: 14/795,293

(22) Filed: Jul. 9, 2015

(65) Prior Publication Data
US 2017/0011535 A1    Jan. 12, 2017

(51) Int. Cl.
*G06K 9/00* (2006.01)
*G06T 11/00* (2006.01)
(Continued)

(52) U.S. Cl.
CPC ............ *G06T 11/008* (2013.01); *A61B 6/032* (2013.01); *A61B 6/14* (2013.01); *A61B 6/4085* (2013.01); *A61C 13/0004* (2013.01); *G06T 5/002* (2013.01); *G06T 7/0012* (2013.01); *G06T 15/08* (2013.01); *G06T 15/40* (2013.01); *G06T 2200/04* (2013.01); *G06T 2207/10081* (2013.01); *G06T 2207/30036* (2013.01); *G06T 2207/30196* (2013.01)

(58) Field of Classification Search
None
See application file for complete search history.

(56) References Cited

U.S. PATENT DOCUMENTS

| | | |
|---|---|---|
| 5,636,255 A | 6/1997 | Ellis |
| 5,839,440 A | 11/1998 | Liou et al. |
| (Continued) | | |

FOREIGN PATENT DOCUMENTS

| | | |
|---|---|---|
| DE | 102012211518 A1 | 6/2013 |
| WO | 9732522 A1 | 9/1997 |
| (Continued) | | |

OTHER PUBLICATIONS

European Search Report dated Mar. 17, 2017, in European Patent Application No. 16178765.0.

*Primary Examiner* — Atiba O Fitzpatrick
(74) *Attorney, Agent, or Firm* — Fitzpatrick, Cella, Harper & Scinto

(57) ABSTRACT

A method, apparatus, and computer readable medium for removing an unwanted object from an image volume are provided. Volumetric data of an object of study is generated in a radiographic scan. Volumetric data of the unwanted object is obtained. The two sets of volumetric data are registered in a common coordinate system. The unwanted object is removed from the volumetric data of the object of study to create modified volumetric data of the object of study. Data from voxels surrounding the removed unwanted object may be used to populate voxels corresponding to the unwanted object with interpolated data. A plurality of forward projections are performed on the modified volumetric data of the object of study, and a tomogram with the unwanted object removed is constructed.

20 Claims, 28 Drawing Sheets

(51) Int. Cl.
  *G06T 15/08*   (2011.01)
  *G06T 15/40*   (2011.01)
  *G06T 5/00*    (2006.01)
  *G06T 7/00*    (2017.01)
  *A61B 6/03*    (2006.01)
  *A61B 6/14*    (2006.01)
  *A61B 6/00*    (2006.01)
  *A61C 13/00*   (2006.01)

(56)                References Cited

U.S. PATENT DOCUMENTS 6,975,697  B2    12/2005  Kasperl et al.
  7,822,251  B2    10/2010  Ding
  2008/0192997 A1*  8/2008  Grass ................... G06T 11/008
                                                        382/128
  2011/0255765 A1* 10/2011  Carlson ............... A61B 5/0064
                                                        382/131
  2013/0022251 A1   1/2013  Chen et al.
  2014/0270440 A1   9/2014  Inglese et al.
  2015/0305702 A1* 10/2015  Sakimoto .............. A61B 6/025
                                                        382/131

FOREIGN PATENT DOCUMENTS

WO       03062856 A1    7/2003
  WO    2010/023665 A2    3/2010
  WO    2013/092744 A1    6/2013
  WO    2014/145591 A2    9/2014

* cited by examiner

| 5 | 5 | 5 | 0 |
|---|---|---|---|
| 5 | 25 | 25 | 5 |
| 5 | 25 | 25 | 5 |
| 5 | 5 | 5 | 0 |

| 5 | 5 | 5 | 0 |
|---|---|---|---|
| 5 | 0 | 0 | 5 |
| 5 | 0 | 0 | 5 |
| 5 | 5 | 5 | 0 |

FIG. 22E

| $X_{14}$ | $X_{24}$ | $X_{34}$ | $X_{44}$ |
|---|---|---|---|
| $X_{13}$ | $Y_2$ | $Y_4$ | $X_{43}$ |
| $X_{12}$ | $Y_1$ | $Y_3$ | $X_{42}$ |
| $X_{11}$ | $X_{21}$ | $X_{31}$ | $X_{41}$ |

FIG. 22F $$Y_1 = \frac{X_{12} + Y_2 + Y_3 + X_{21}}{4}$$

$$Y_2 = \frac{X_{13} + X_{24} + Y_4 + Y_1}{4}$$

$$Y_3 = \frac{Y_1 + Y_4 + X_{42} + X_{31}}{4}$$

$$Y_4 = \frac{Y_2 + X_{34} + X_{43} + Y_3}{4}$$

FIG. 22G

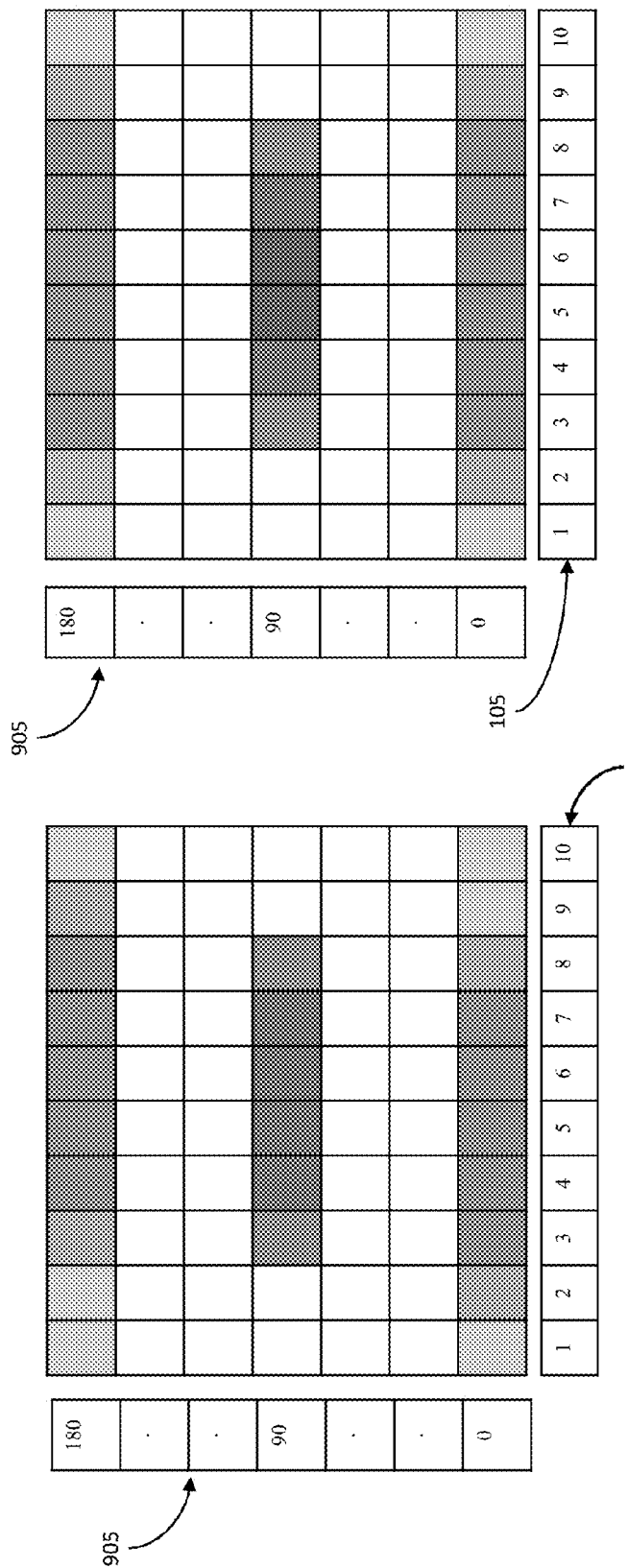

METHOD, APPARATUS, AND COMPUTER READABLE MEDIUM FOR REMOVING UNWANTED OBJECTS FROM A TOMOGRAM

BACKGROUND OF THE INVENTION

Field of the Invention

This application relates to managing objects that produce artifacts in a tomogram.

Description of Related Art

Unfortunately, many individuals will eventually need filings, bridges, implants or the like to repair or replace damaged teeth. These restoration pieces must be customized to each patient's unique anatomical layout. In the past, clinicians have used study models, wax-ups, and panoramic x-rays to obtain information about a patient's anatomy. This information dictates how the dental implants are prepared, and thus the success of the patient's treatment is heavily dependent on the accuracy of these tools.

One technique used to obtain anatomical information is Cone Beam Computer Tomography (CBCT) which can produce a three-dimensional (3D) image (a tomogram) of an image volume corresponding to a particular region of interest in a patient. While CBCT presents many advantages there are drawbacks. For example, one drawback is the occurrence of noise and artifacts in the images due to unwanted objects which are irrelevant to the diagnostic application. For example, a patient may have a metal retainer affixed to the teeth which cannot be easily removed for a scan. Another example is a bite-block which a patient bites down on to remain still during the scan. Each of these objects may produce artifacts in the 3D image volume data (also referred to as volumetric data) and those artifacts may appear in the resulting 3D image, impairing the ability of a clinician to make an accurate model. Another drawback is that an unwanted object in close proximity to an anatomical feature of interest may obscure the anatomical feature of interest thus degrading the efficacy of the tomogram. While there are known techniques to completely remove certain objects from volumetric data, such techniques have been unable to account for materials where the attenuation coefficient ($\mu$) of the unwanted object (e.g. a plastic bite plate) is close to the attenuation coefficient of an object of interest. Thus, it would be beneficial to have an improved technique for removing unwanted objects (and their negative effects) from a tomogram.

BRIEF DESCRIPTION OF THE DRAWINGS

FIGS. 22A-22G are illustrations of one method of populating pixels corresponding to a removed unwanted object with interpolated data.

FIGS. 26A-26B are illustrations of sinograms respectively corresponding to the beam intensities calculated during a forward projection.

SUMMARY OF THE INVENTION

In one example embodiment, a method is provided that includes registering, removing, performing, and constructing steps. First volumetric data, corresponding to an image volume comprising an object of study and an unwanted object, and second volumetric data, corresponding to the unwanted object are registered in a common coordinate system in the registering step. The unwanted object is removed from the first volumetric data to generate modified first volumetric data in the removing step. A plurality of forward projections are performed on the modified first volumetric data to generate a plurality of planar projection images in the performing step. A three-dimensional image of the image volume is constructed from the plurality of planar projection images, such that the three-dimensional image does not contain the unwanted object.

In another embodiment, an apparatus that includes a processor and a memory storing a control program is provided. The processor and the memory are configured to (i) register first volumetric data, corresponding to an image volume comprising an object of study and an unwanted object, and second volumetric data, corresponding to the unwanted object, in a common coordinate system; (ii) remove the unwanted object from the first volumetric data to generate modified first volumetric data; (iii) perform a plurality of forward projections on the modified first volumetric data to generate a plurality of planar projection images; and (iv) construct a three-dimensional image of the image volume from the plurality of planar projection images, such that the three-dimensional image does not contain the unwanted object.

In a further embodiment, a non-transitory computer readable storage medium storing a computer program for causing a computer to execute a method is provided. The method includes registering, removing, performing, and constructing steps. First volumetric data, corresponding to an image volume comprising an object of study and an unwanted object, and second volumetric data, corresponding to the unwanted object are registered in a common coordinate system in the registering step. The unwanted object is removed from the first volumetric data to generate modified first volumetric data in the removing step. A plurality of forward projections are performed on the modified first volumetric data to generate a plurality of planar projection images in the performing step. A three-dimensional image of the image volume is constructed from the plurality of planar projection images, such that the three-dimensional image does not contain the unwanted object.

DETAILED DESCRIPTION OF THE INVENTION

Figure 1:
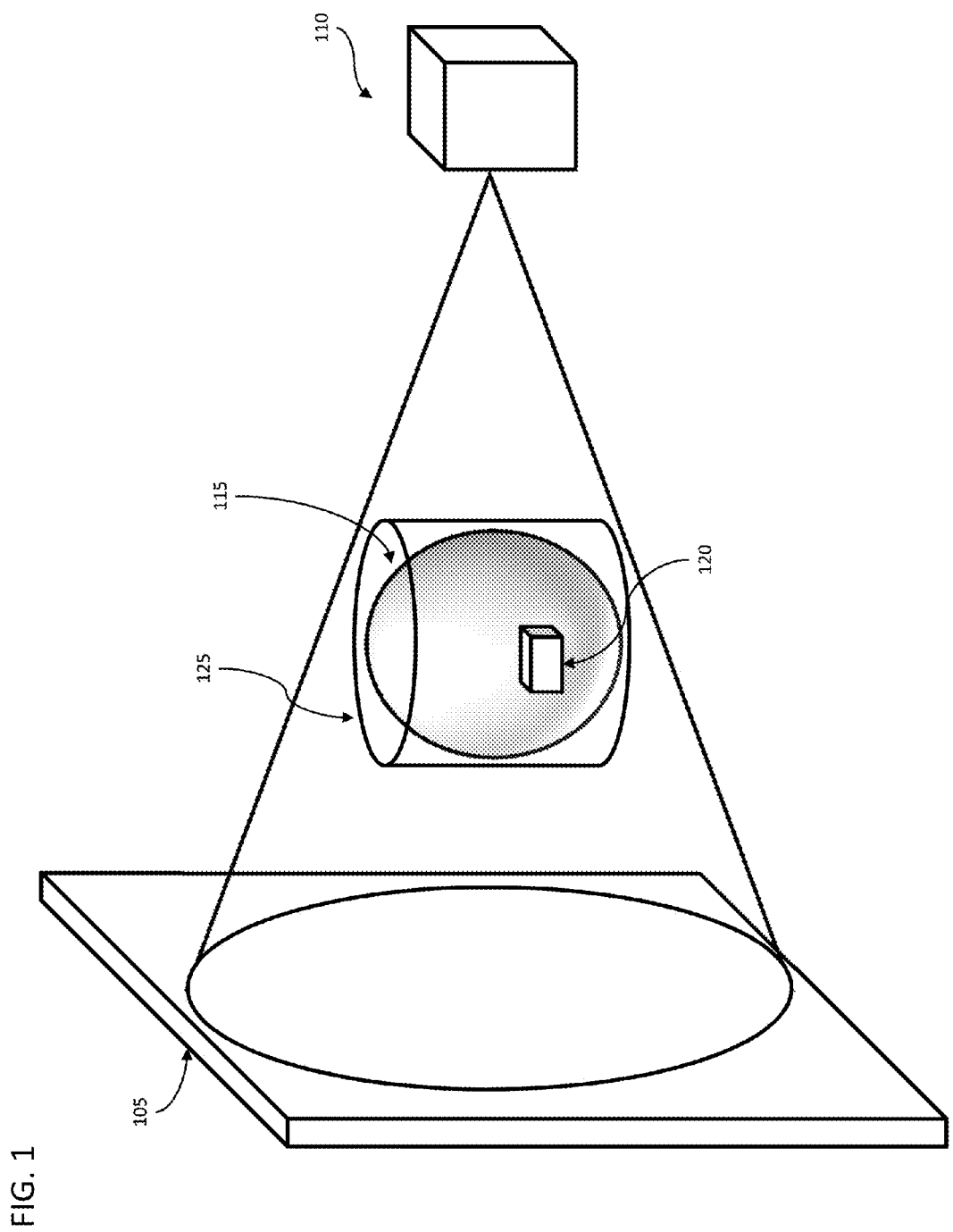
FIG. 1 is an overview of a CBCT imaging apparatus.

FIG. 1 is an illustration of a CBCT system according to one example embodiment herein. While a CBCT system is described herein, the systems and techniques described herein are not limited to CBCT, but may be used in other types of radiography including x-ray based tomography systems such as computed tomography (CT)

As shown in FIG. 1, a radiographic source 110 (hereinafter "source"), such as an x-ray source, projects a beam of ionizing radiation which is incident on a radiographic detector 105 (hereinafter "detector") after traveling through an image volume 125. The beam of ionizing radiation may be of different shapes such as pyramid-shaped or cone-shaped. To create a tomogram (a 3D image) of the image volume 125, the detector 105 and source 110 may be rotated through at least 180 degrees angular range while a plurality of exposures are recorded by the detector 105 during that span. In one example herein, the image volume 125 is that portion of space through which ionizing radiation passes during each exposure and may be represented as a cylindrical volume (although this example is not limiting). An object of study 115 (e.g., a patient) is positioned within the image volume 125. In the illustrated example, an object 120 that is not desired to be included in the image is contained within the object of study 115. The unwanted object 120 may be a bite-block, a retainer, or a previous dental restoration piece, for example.

Figure 2:
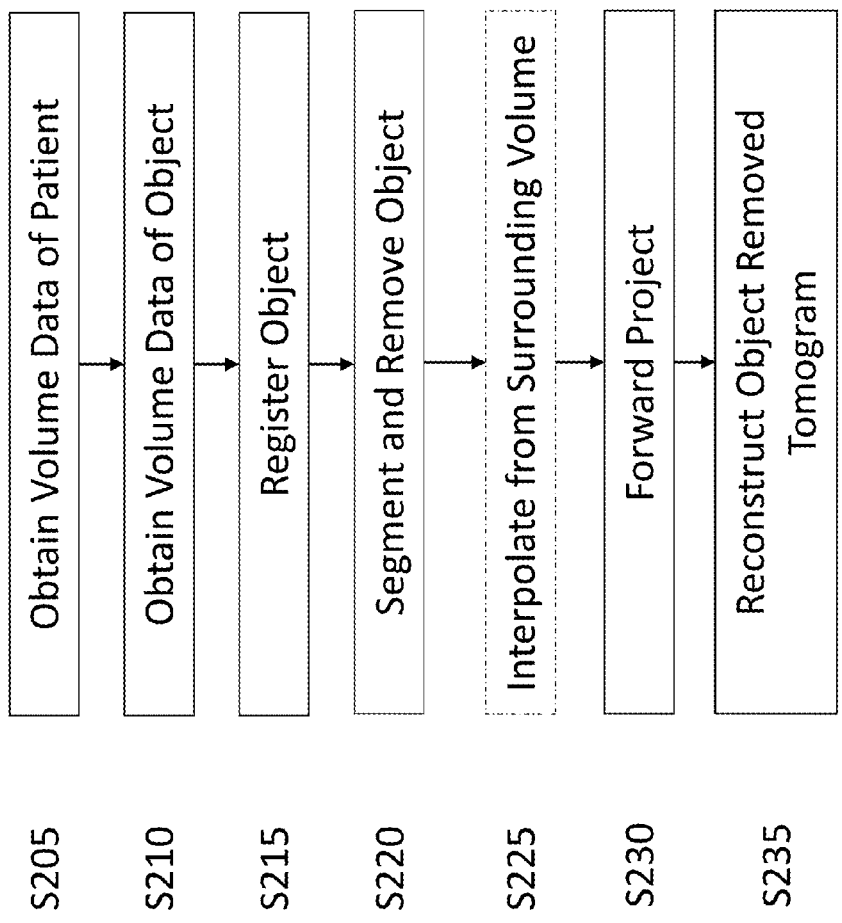
FIG. 2 is a flowchart illustrating steps of removing an unwanted object according to an exemplary embodiment.

FIG. 2 is a flowchart illustrating a method for removing the unwanted object 120 from a tomogram of the object of study 115, according to one example embodiment herein. Briefly, volumetric data of the object of study 115 is obtained, with the unwanted object 120 contained therein (S205). In one example, volumetric data is a three dimensional array of data, with each element in the array corresponding to a volume element (voxel) within the image volume. Each element in the three-dimensional array holds a data value representing an amount of beam attenuation corresponding to that voxel. Next, volumetric data of the unwanted object 120 is obtained (S210). The volumetric data of the object of study 115 and the volumetric data of the unwanted object 120 are then registered in a common coordinate system (S215). As discussed below, registration may, in one example, occur through an iterative process of translating and rotating one set of volumetric data with respect to the other, comparing a difference between the two sets of volumetric data, and determining if the difference is an absolute minimum. The unwanted object 120 is then segmented and removed from the volumetric data of the object of study 115 to create modified volumetric data, that does not include a representation of the unwanted object 120 (S220). In one example, the removal may be accomplished by subtracting volumetric data of the unwanted object 120 from the volumetric data of the object of study 115. In one embodiment, the unwanted object 120 may be replaced by interpolated data from the region surrounding the unwanted object (S225). As described below, in one embodiment, data from voxels surrounding the unwanted object 120 may be weighted and used to replace data corresponding to the unwanted object 120. A series of virtual forward projections through the image volume 125 are then made to create a series of virtual two-dimensional (2D) planar projections from the modified volumetric data (S230). From the 2D planar projections, a tomogram can be constructed by back projecting filtered sinograms respectively corresponding to the planar projections (S235). Each of these steps will be described in more detail below.

To obtain volumetric data of the object of study 115 (S205), the detector 105 and source 110 are rotated about the image volume 125 while a series of exposures are recorded by the detector 105 during the rotation. In one example embodiment, the detector 105 and source 110 are rotated at least 180°. Typically, a full 360° rotation is not performed because data obtained in the second half of the rotation is symmetrical to data obtained in the first half of the rotation. The recorded exposures are sequential planar projection images captured within the field of view of the detector 105. As one of ordinary skill will appreciate in view of FIG. 1, the field of view of the detector 105 depends on the size of the detector 105, but is typically larger than the planar projection of the beam of ionizing radiation incident on the detector 105 to ensure that all radiation which travels through the imaging volume is incident on the detector 105.

Thus, as shown in FIG. 1, in one example some portions of the detector 105 do not receive ionizing radiation.

A planar projection image is a two-dimensional (2D) data array the values of which represent the intensity of the radiation beam received by the detector 105. In general, radiation propagating through a material is attenuated in proportion to the attenuating properties of the material through which it passes, often referred to as the attenuation coefficient (μ). Thus, the amount of material and the attenuation coefficient (μ) of the material determine the reduction in beam intensity. The reduced intensity beam is incident on the detector 105 and recorded. Of course, if different materials are present, then the amount of the respective materials and their respective attenuation coefficients (μ) determine the intensity of the beam incident on the detector 105.

The 2D planar projection images are used to construct a tomogram of the image volume 125. The tomogram is a visual representation of the volumetric data of the image volume 125. The volumetric data contains a plurality of values respectively corresponding to a plurality of individual volume elements (voxels). Reconstruction algorithms, such as, for example, the filtered backprojection (FBP) algorithm, may be used to generate the tomogram from the planar projection images. As discussed above, however, if an unwanted object, such as object 120, is present in each of the 2D planar projection images, several issues may arise. First, if the unwanted object has a substantially similar attenuation coefficient to the surrounding tissue, the reconstruction algorithm may have difficulty distinguishing between the two materials. As such, the resulting tomogram may show the two separate materials (or separate objects) as the same object, or one may even obscure the view of the other. Second, image artifacts from the unwanted object 120 may be generated by the reconstruction algorithm and appear in the resulting tomogram. This is especially true in a case where the unwanted object is a metallic object which scatters the radiation beam. Metallic objects may also have such a high attenuation factor that the intensity of the radiation beam incident on the detector is below the noise threshold of the detector. As a result, invalid data is used for the reconstruction process. Thus, it may be preferable to remove the unwanted object completely and treat the volume of space it occupied as empty space, or to interpolate data from surrounding voxels to replace the unwanted object.

Having described a general CBCT system, such as the one illustrated in FIG. 1, and outlined an exemplary method of removing an unwanted object 120, we will now discuss in more detail each of the steps illustrated in FIG. 2. First, however, a representative CBCT system used to illustrate the exemplary method shown in FIG. 2 will be discussed.

Figure 3:
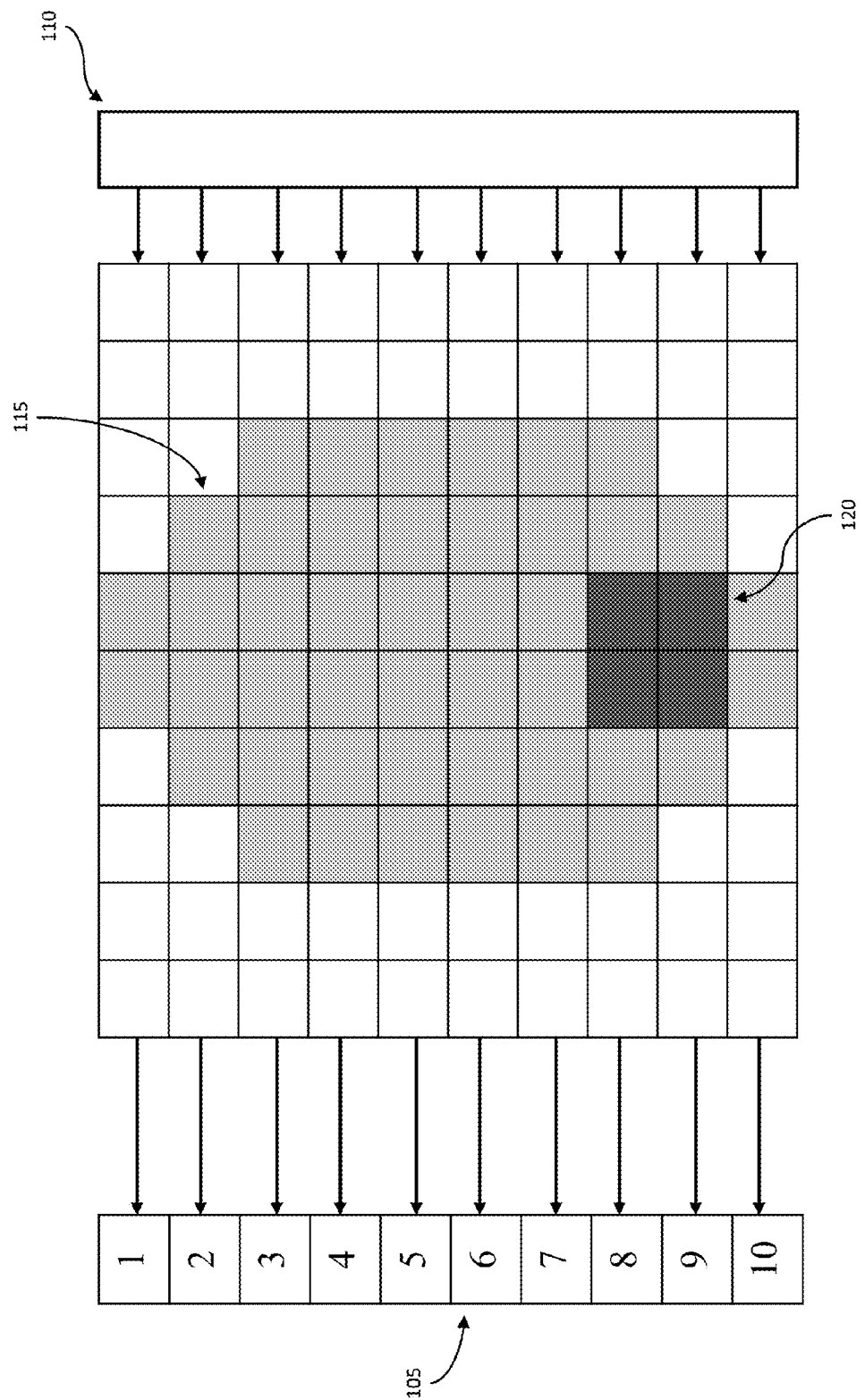
FIG. 3 is an illustration of radiation passing through an image volume when the imaging apparatus is at a first position.
Figure 4:
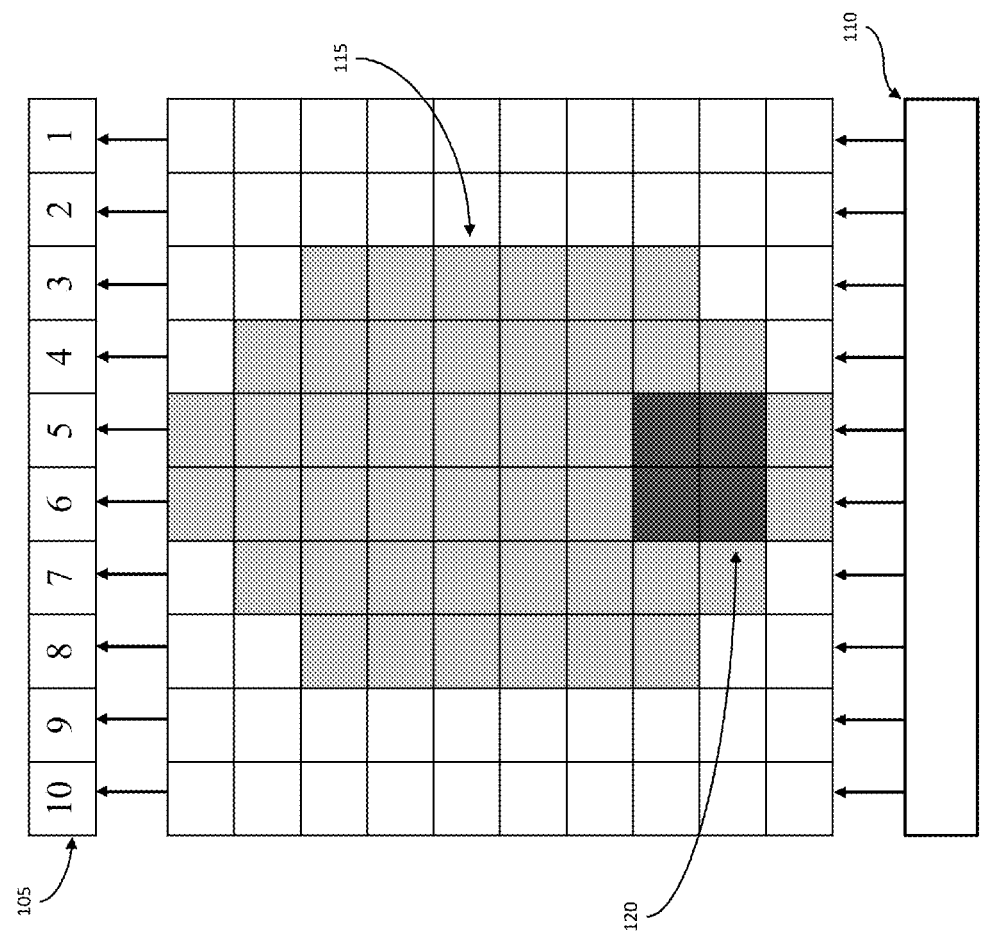
FIG. 4 is an illustration of radiation passing through an image volume when the imaging apparatus is at a second position.
Figure 5:
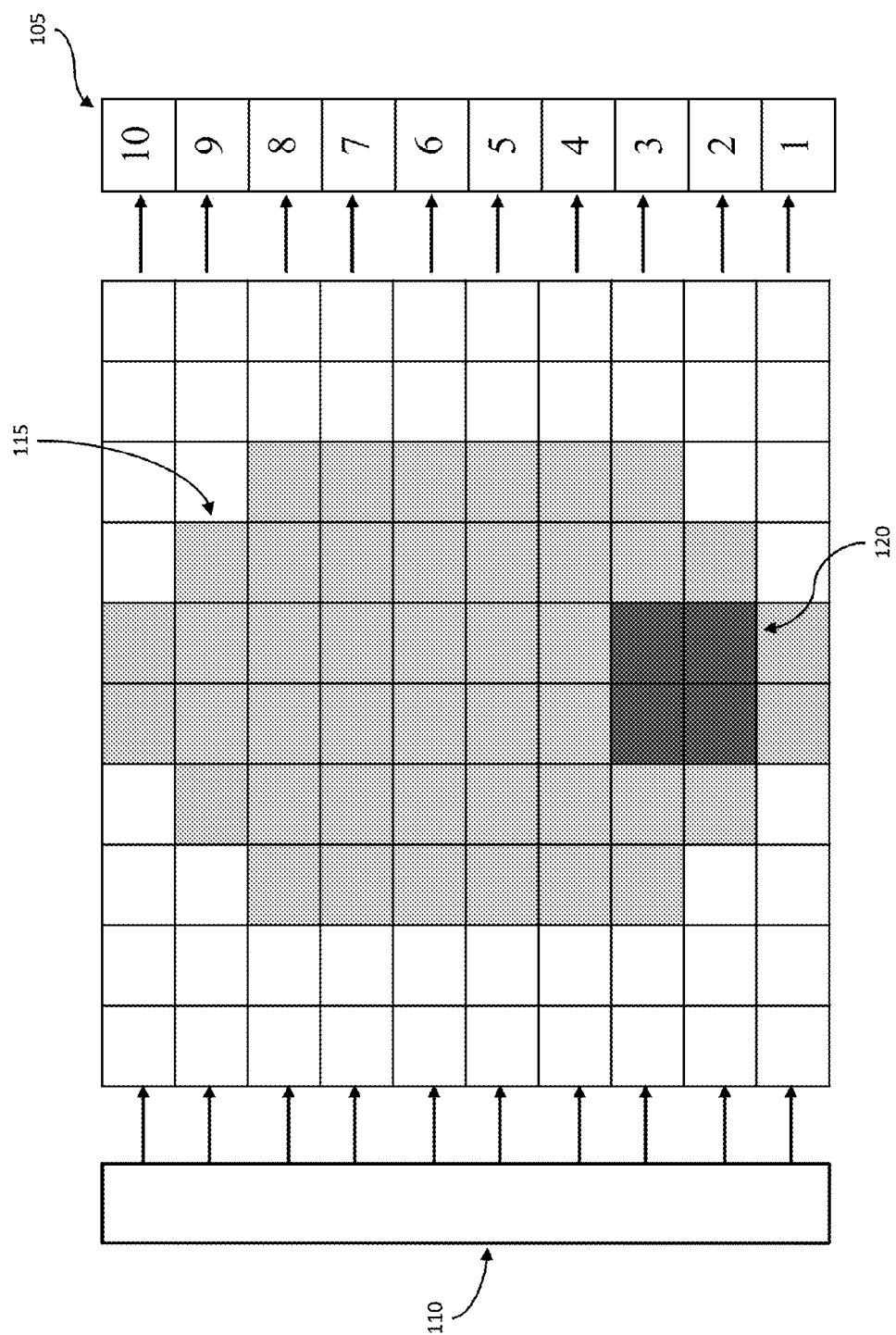
FIG. 5 is an illustration of radiation passing through an image volume when the imaging apparatus is at a third position.

FIGS. 3-5 are 2D representations of a CBCT system during the generation of volumetric image data at three different angular positions (0°, 90°, and 180°). In FIGS. 3-5 only ten detector elements of detector 105, are shown. As shown above in FIG. 1, however, the detector 105 is a two-dimensional array of detector elements, and may include hundreds or thousands of individual detector elements. In one example, the ten detector elements shown in FIGS. 3-5 may represent at least part of a line of detector elements located near the center of the detector 105. Second, the ionizing radiation is shown as a series of parallel lines through the image volume 125 (represented by the parallel lines emanating from source 110 and entering detector 105). In a CBCT system, a cone of ionizing radiation propagates through the image volume 125, and thus not all of the lines of radiation are parallel to each together. Nevertheless, a parallel representation is appropriate for illustrating radiation propagating through a center portion of the image volume 125 and which is incident on the center of the detector 105. As one of ordinary skill will appreciate in view of this description, the representation shown in FIGS. 3-5 is somewhat simplified to provide for ease of explanation.

As noted above, FIGS. 3-5 illustrate the detector 105 and source 110 at positions of 0°, 90°, and 180°, respectively, during the rotation of the detector 105 and source 110 about the object of study 115. As discussed above, a planar projection image is recorded by the detector 105 at each position. More specifically, the detector 105 records the intensity of radiation incident thereon. Since the radiation is attenuated by the material absorbed by matter through which it passes, the intensity of the radiation incident on the detector 105 is less than the intensity of the radiation that leaves the source 110. Thus, the intensity of the radiation incident on the detector 105 may be expressed as a percentage of the original intensity. An object of study 115 is disposed within the imaging volume 125 and contains an unwanted object 120. In this example, the unwanted object 120 has a higher attenuation coefficient than the object of study 115, as indicated by the four darker pixels 120 (the two-dimensional counterpart of a voxel) in FIGS. 3-5. Of course, the unwanted object could have a lower or even equal attenuation coefficient as well. In the example shown in FIGS. 3-5, a beam of radiation will be attenuated to a greater degree passing through the unwanted object 120 as compared with the object 115.

Figure 6:
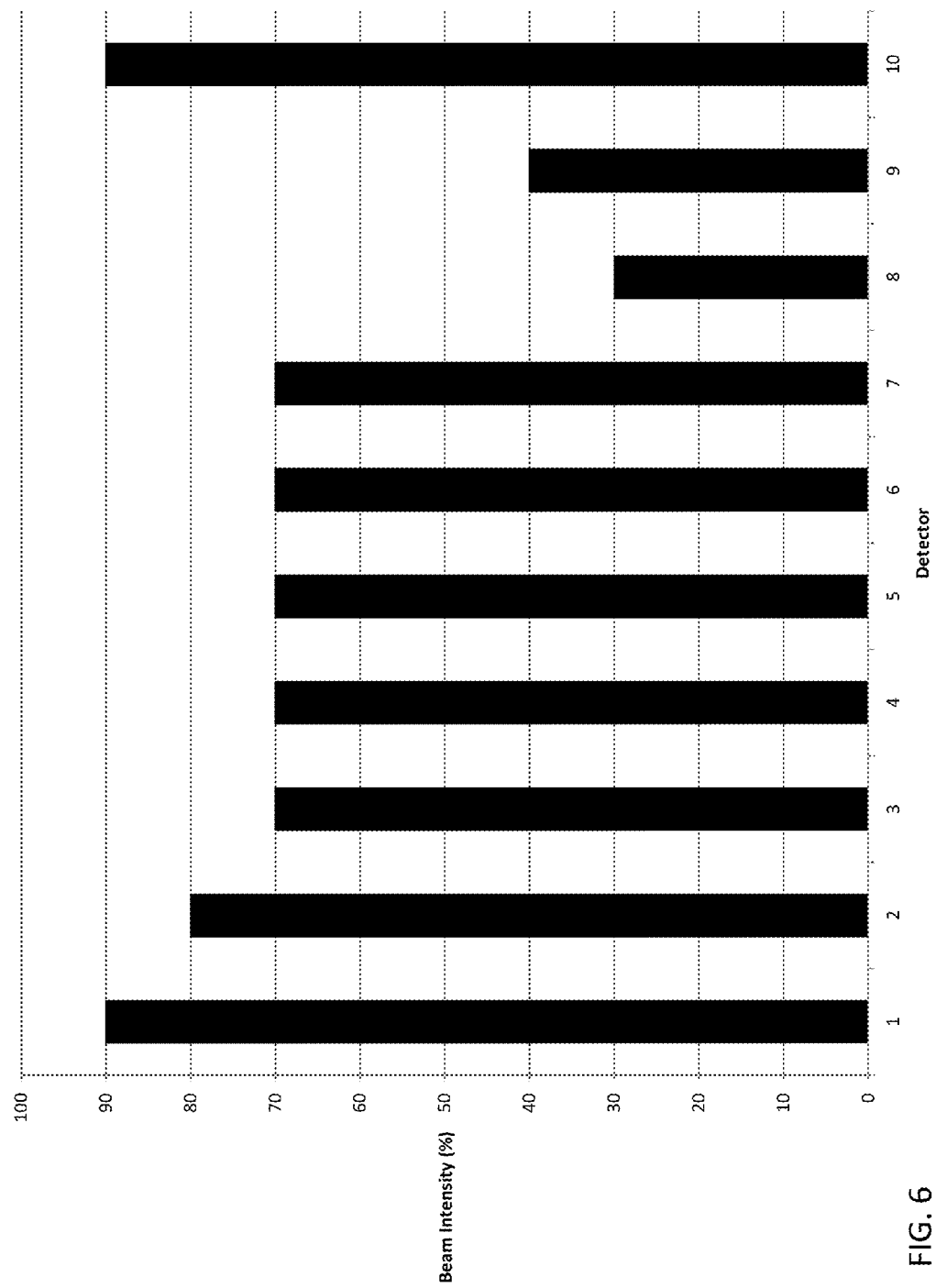
FIG. 6 is a graph of beam intensity for respective detector elements when the imaging apparatus is at the first position.
Figure 7:
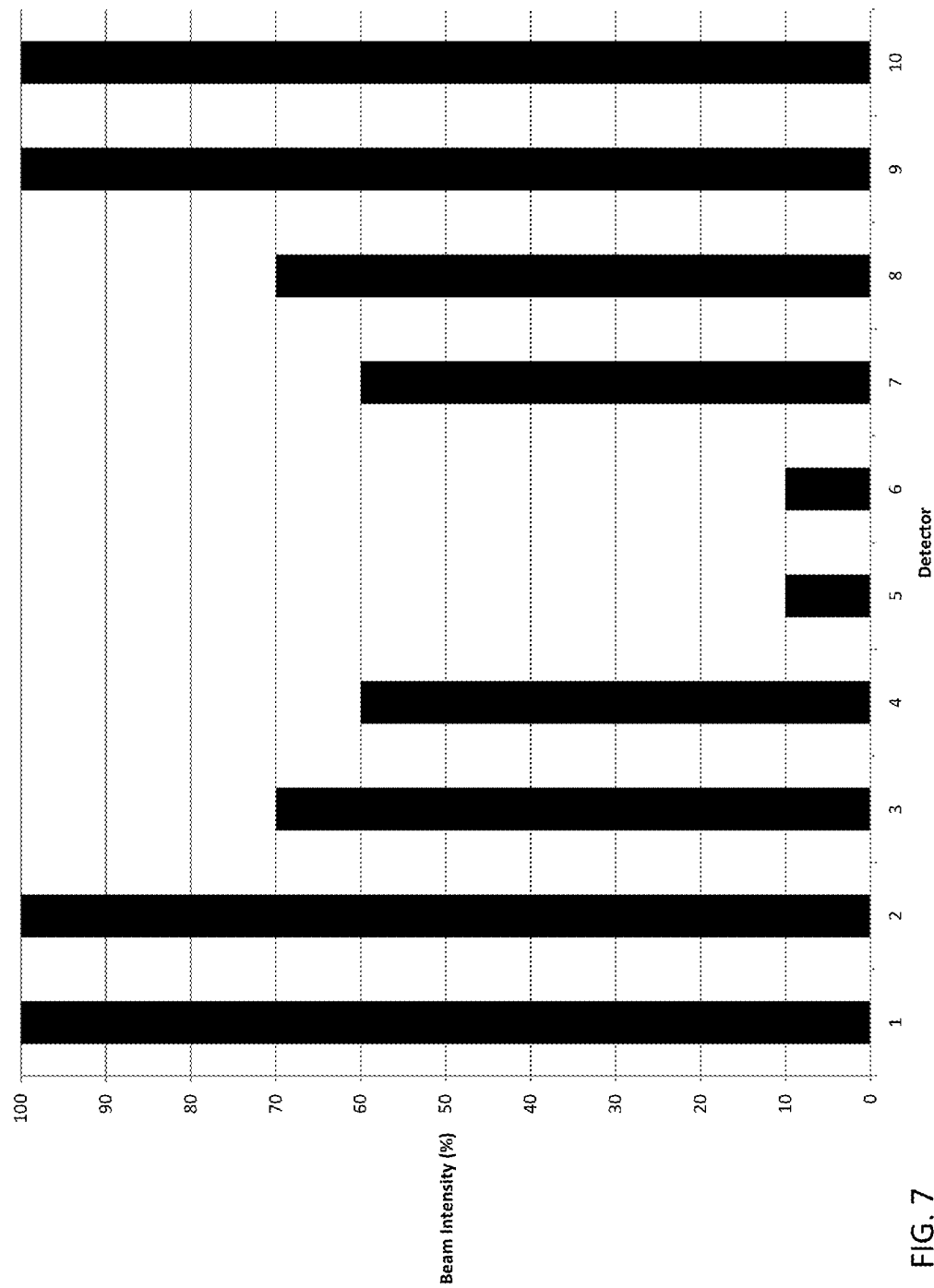
FIG. 7 is a graph of beam intensity for respective detector elements when the imaging apparatus is at the second position.
Figure 8:
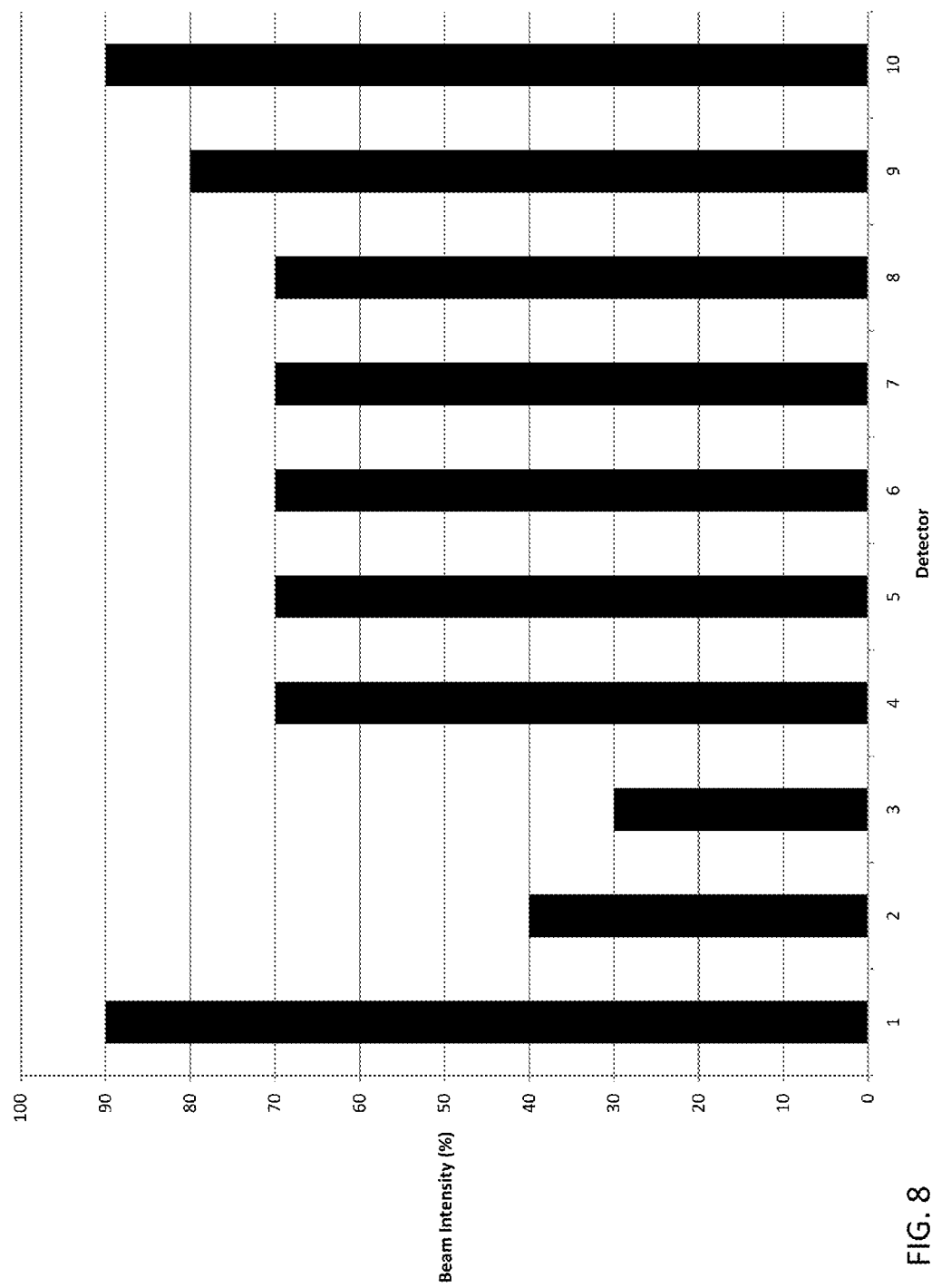
FIG. 8 is a graph of beam intensity for respective detector elements when the imaging apparatus is at the third position.

FIGS. 6-8 are graphs of example beam intensities for each of the detector elements (1-10) at positions of 0°, 90°, and 180°, respectively. As shown in FIG. 3, at 0° beams incident on detector elements 8 and 9 pass through the unwanted object 120 and are attenuated to a greater degree. Thus, as shown in FIG. 6, the beam intensity (expressed as percentage of the original intensity) is lowest for detector elements 8 and 9, in this example. A beam incident on detector element 8 travels through more of object 115 than a beam incident on detector element 9, and thus is attenuated to the greatest extent at 0°, in this example.

In a similar manner, at 90° beams incident on detector elements 5 and 6 pass through the unwanted object 120 and through a greater amount of object 115 than any other beam (see FIG. 4). Thus, as shown in FIG. 7, detector elements 5 and 6 record the lowest beam intensity in this example. At 180° (FIG. 5), beams incident on detector elements 2 and 3 pass through the unwanted object 120 and thus are attenuated to a greater degree. Thus, as shown in FIG. 8, beam intensity is lowest for detector elements 2 and 3 in this example.

Figure 9:
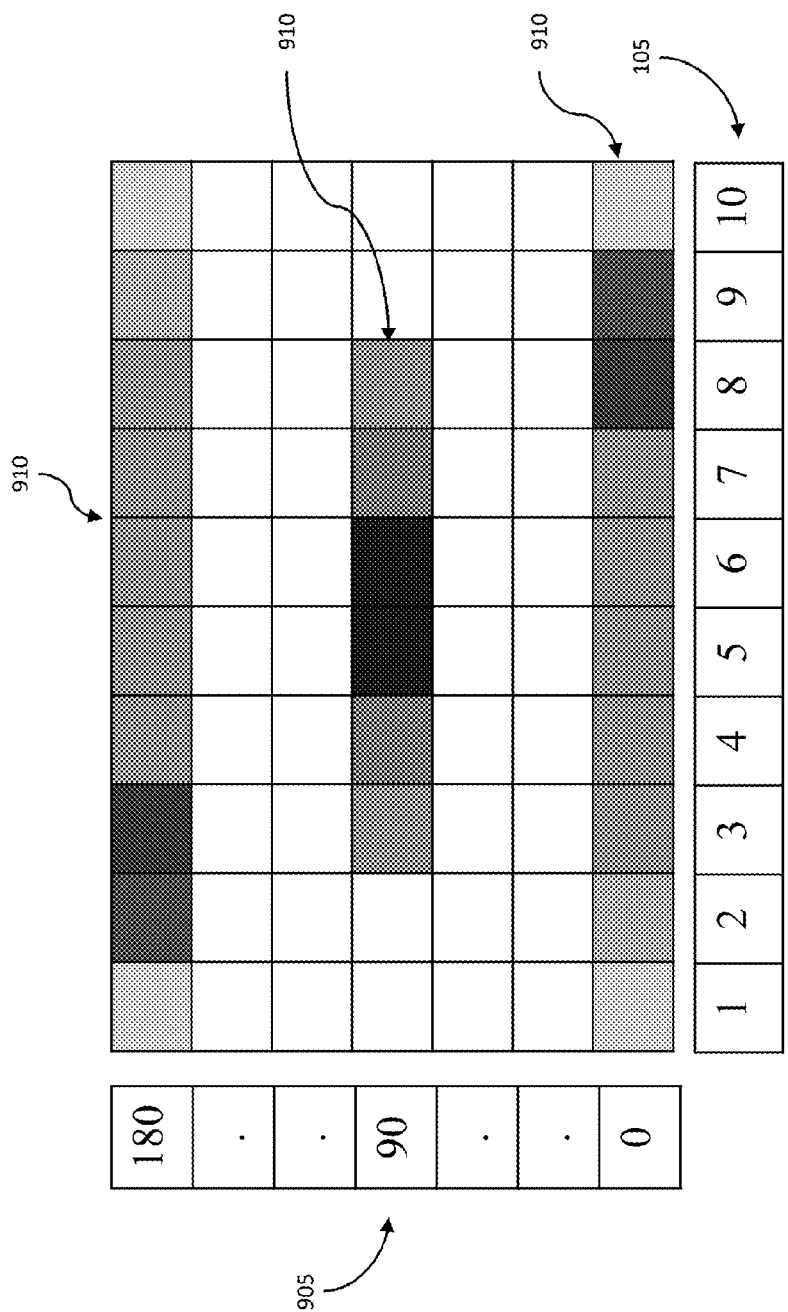
FIG. 9 is a sinogram of an image volume containing an object of study and an unwanted object.

FIG. 9 is a sinogram showing an example of recorded beam intensities at angles 0°, 90°, and 180° graphed in FIGS. 6-8. A sinogram is surface plot of angle 905 (Y-axis), detector element (1-10) (X-axis), and beam intensity 910 (lightness/darkness). While only three exposures are shown in FIG. 9, one of ordinary skill would appreciate that many more exposures can be recorded as the detector 105 and source 110 are rotated about the image volume, and thus FIG. 9 illustrates just some of the recorded exposures. Moreover, one of ordinary skill would also appreciate that a sinogram generated from the two-dimensional planar projections would be a three-dimensional array. The i and j dimensions of the array would represent the location of a particular detector element, while the k dimension of the array would correspond to the angle at which the planar projection was recorded. From this data a computer can generate the volumetric data of the image volume (and the tomogram) using a reconstruction algorithm.

Next, volumetric data of the unwanted object 120 is obtained (S210). This may be accomplished in a variety of ways. First, if the unwanted object 120 can easily be scanned in the CBCT system, then the unwanted object can simply be scanned and the corresponding data processed to obtain the volumetric data. This can be the most convenient method to obtain volumetric data in the case where the unwanted object 120 is, for example, a bite-block that is part of the CBCT system.

Figure 10:
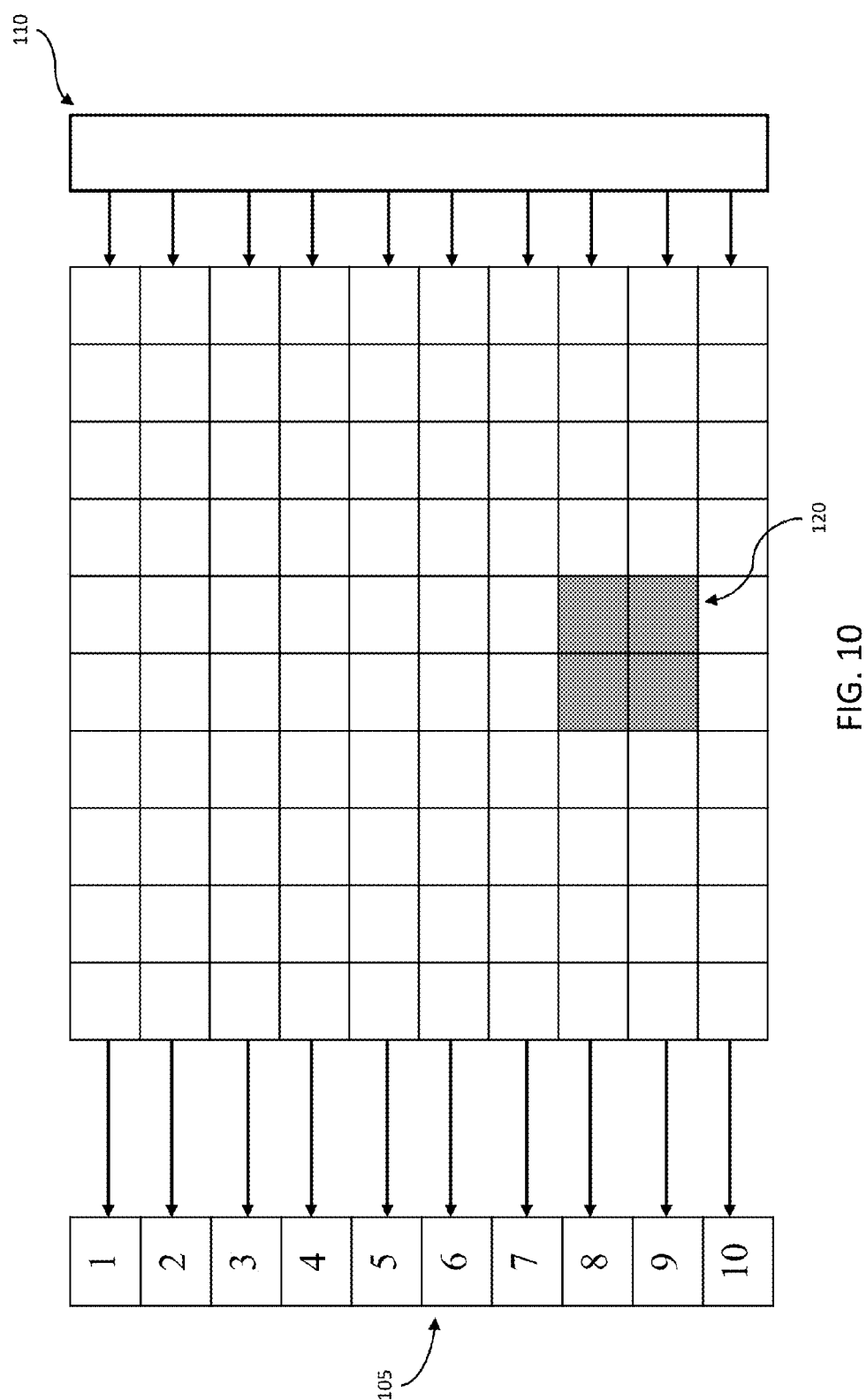
FIG. 10 is another illustration of radiation passing through an image volume when the imaging apparatus is at a first position.
Figure 11:
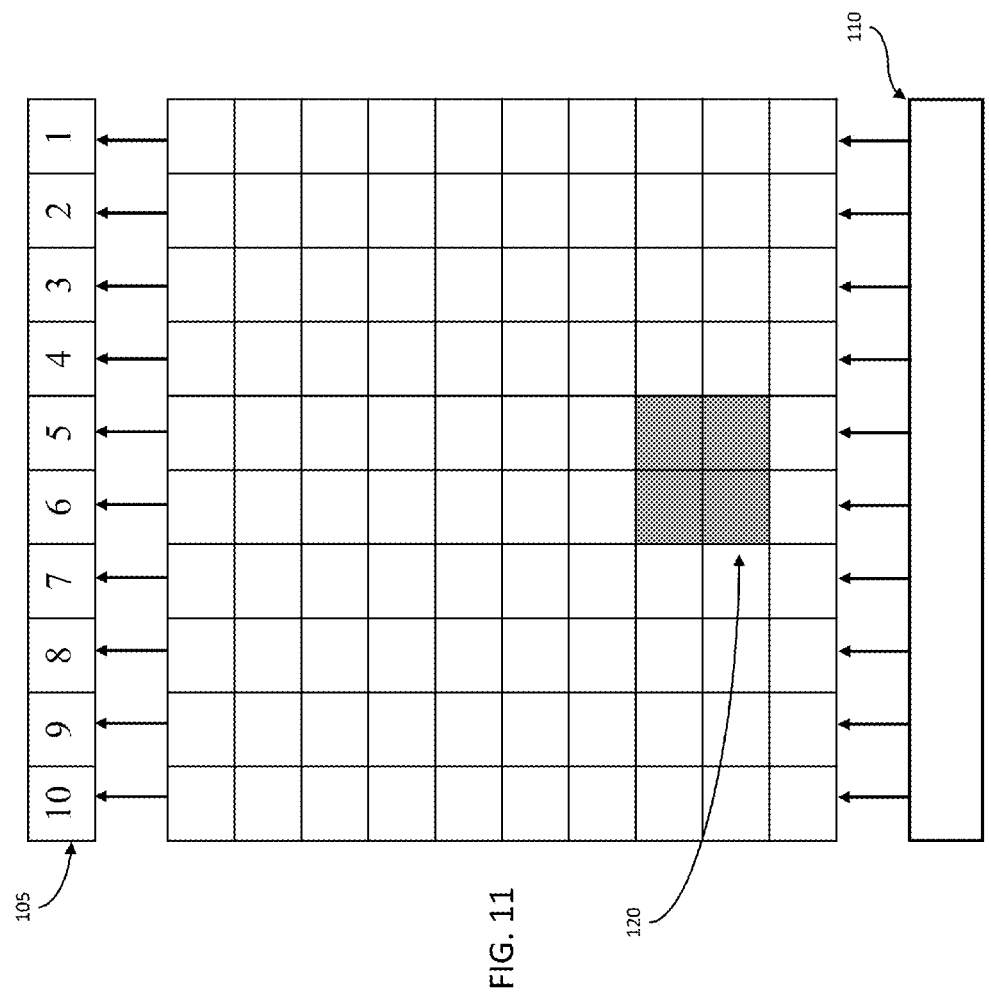
FIG. 11 is another illustration of radiation passing through an image volume when the imaging apparatus is at a second position.
Figure 12:
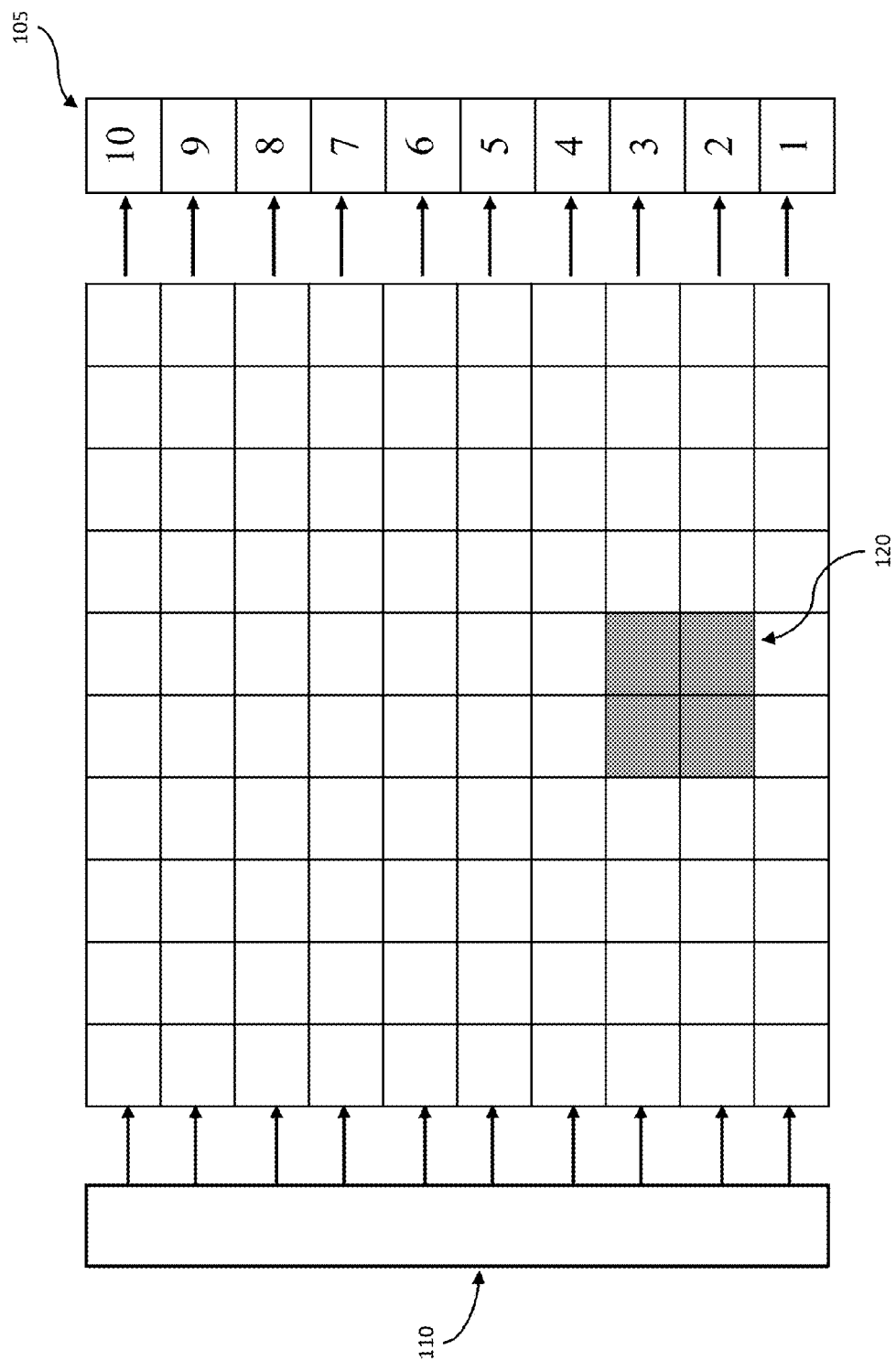
FIG. 12 is another illustration of radiation passing through an image volume when the imaging apparatus is at a third position.
Figure 13:
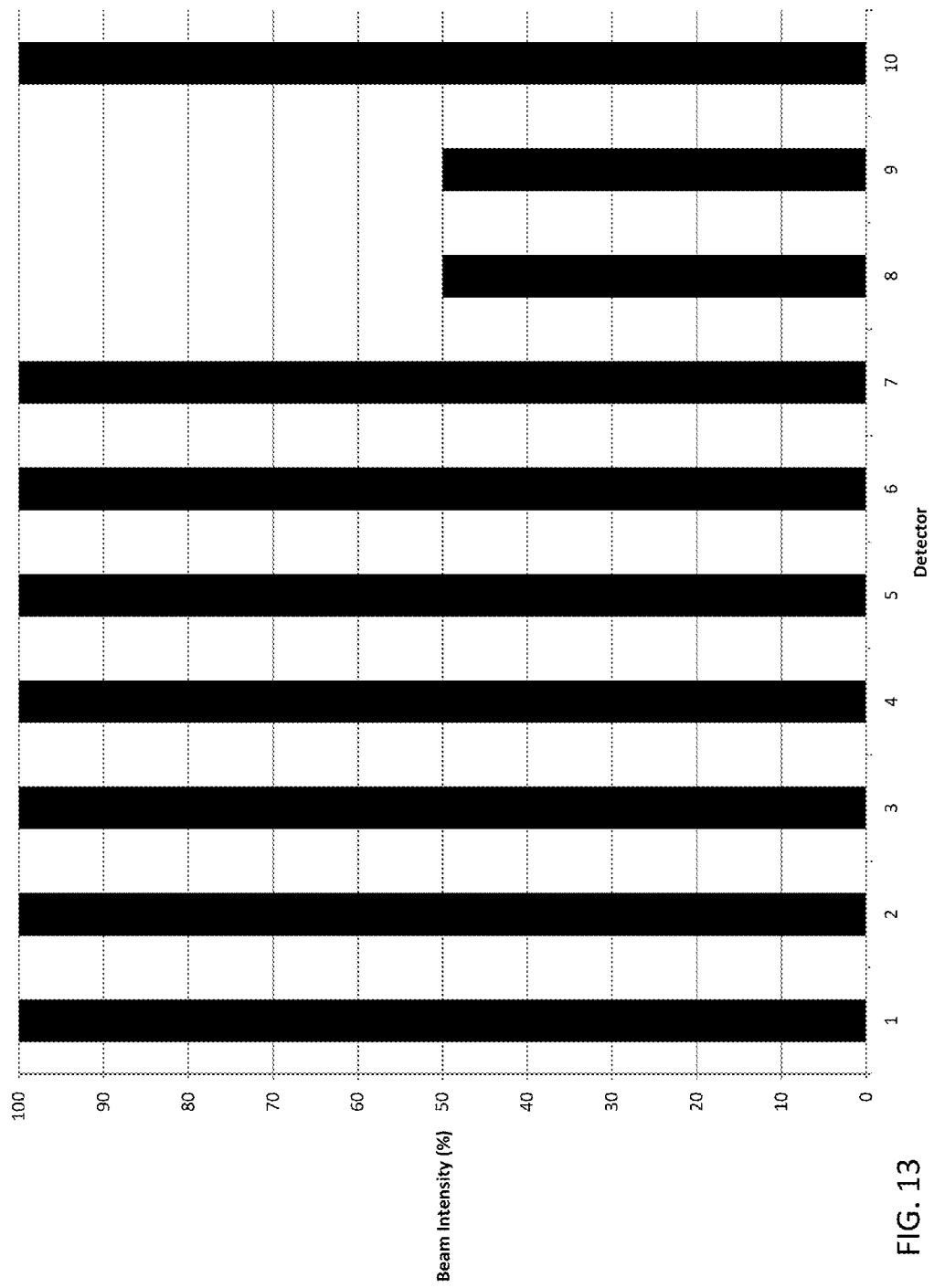
FIG. 13 is another graph of beam intensity for respective detector elements when the imaging apparatus is at the first position.
Figure 14:
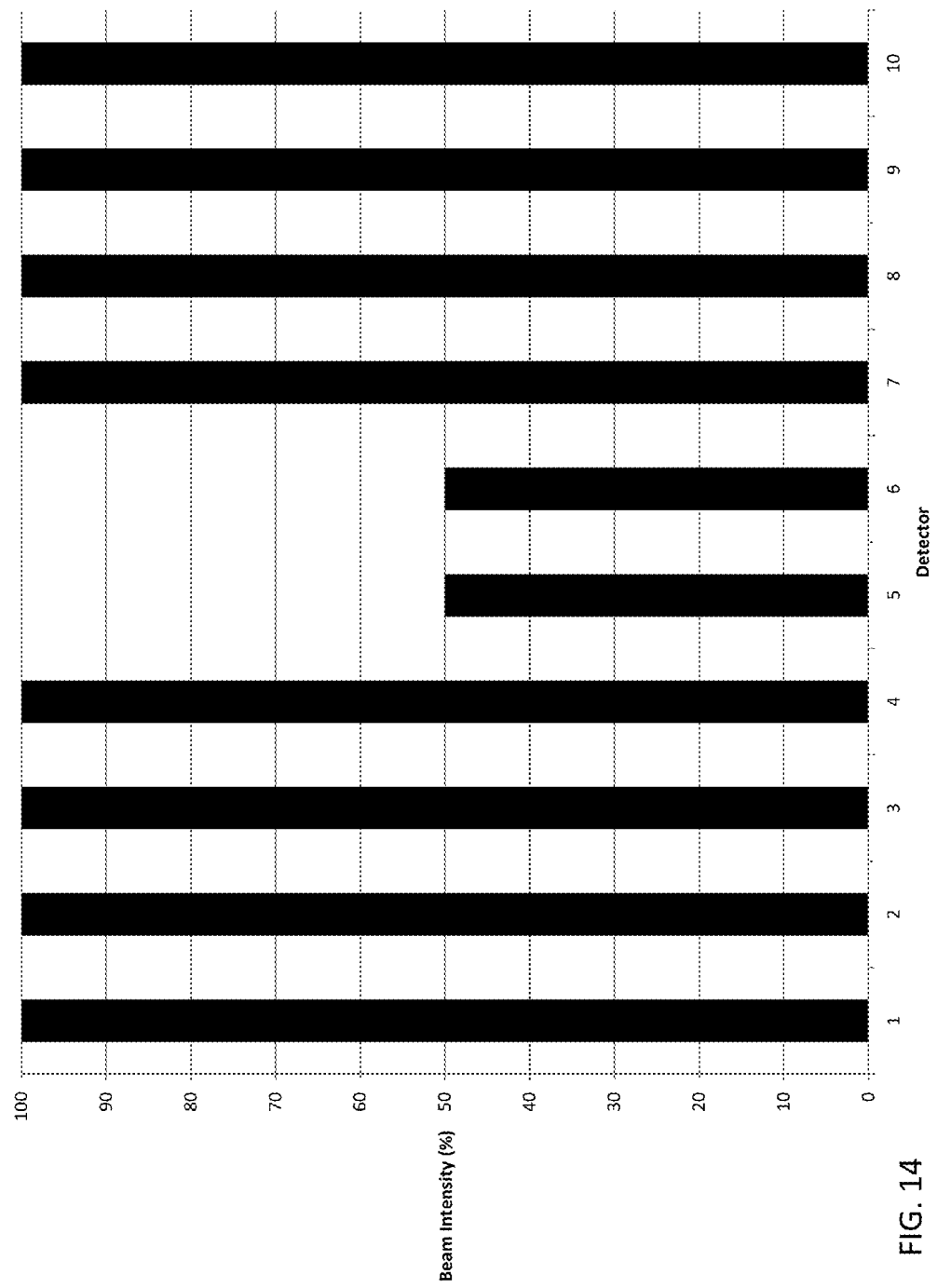
FIG. 14 is another graph of beam intensity for respective detector elements when the imaging apparatus is at the second position.
Figure 15:
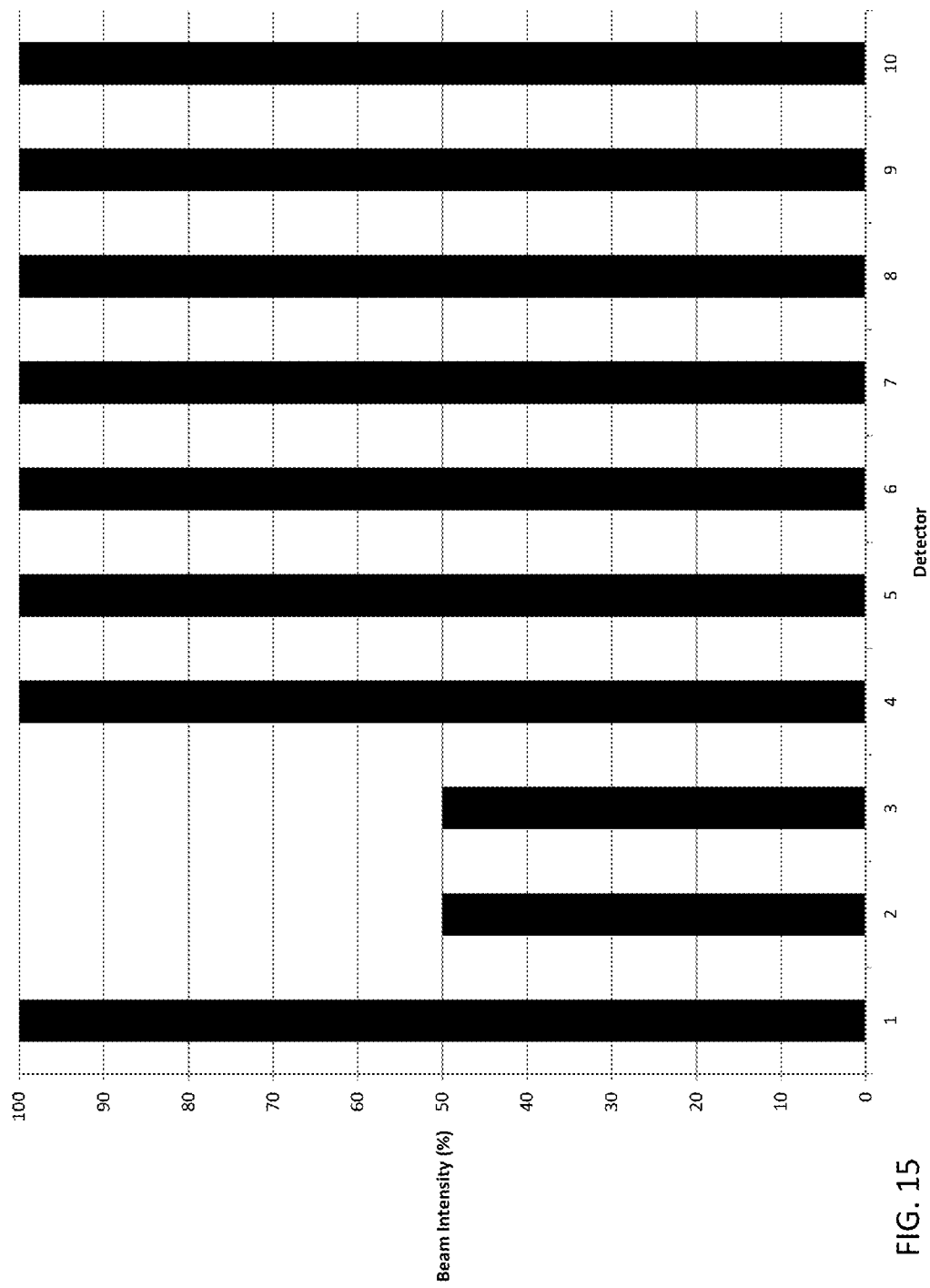
FIG. 15 is another graph of beam intensity for respective detector elements when the imaging apparatus is at the third position.
Figure 16:
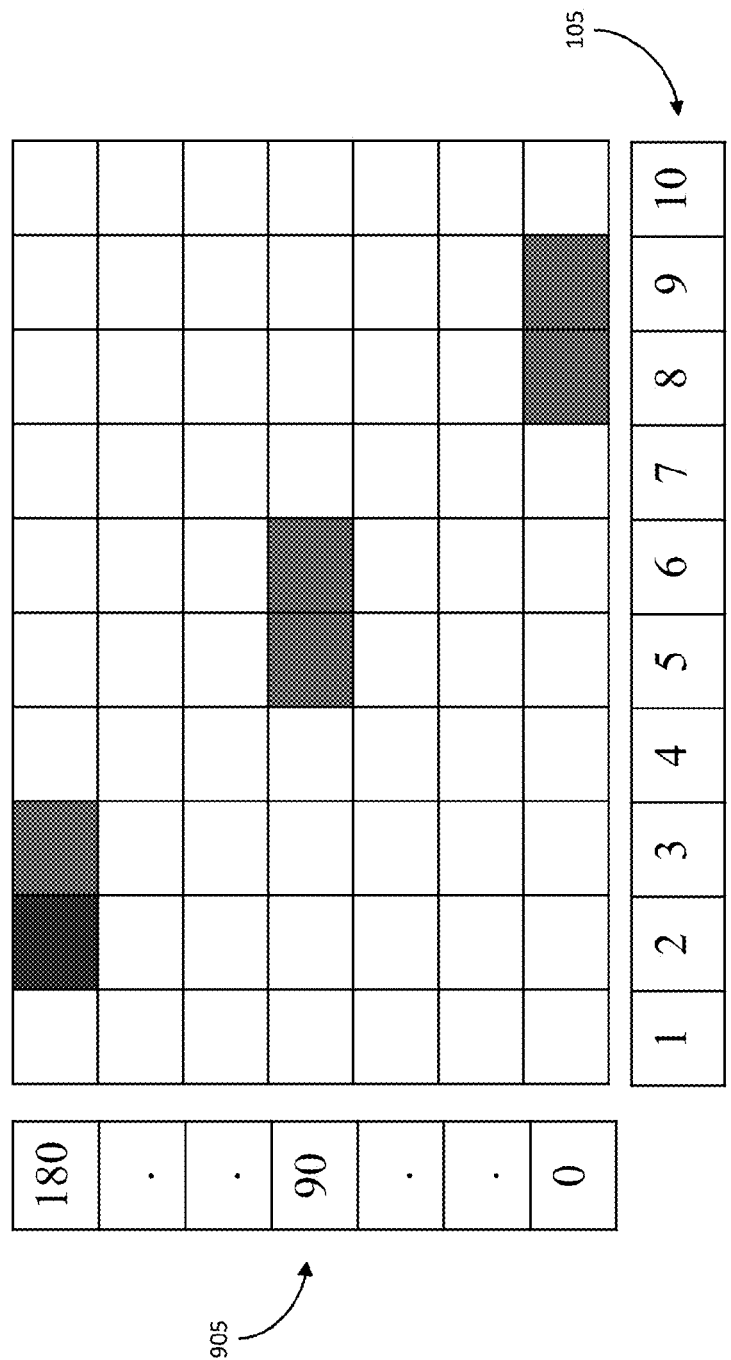
FIG. 16 is a sinogram of an image volume containing the unwanted object.

FIGS. 10-16 are illustrative of this process. In this case, an unwanted object 120 is scanned in a similar manner as the object of study 115. The source 110 and the detector 105 are rotated 180° (in one embodiment), and a plurality of planar projection images are recorded. FIGS. 10-12, show the position of the source 110 and detector 105 are angles 0°, 90°, and 180°, respectively. FIGS. 13-15 show the beam intensity data recorded by the detector at angles 0°, 90°, and 180°, respectively. FIG. 16 is a sinogram produced from the recorded beam intensity data. Here, only data for angles 0°, 90°, and 180° are shown (corresponding to FIGS. 13-15). However, the sinogram can be populated with data recorded from numerous angular positions during the rotation of the source 110 and the detector 105.

Figure 17:
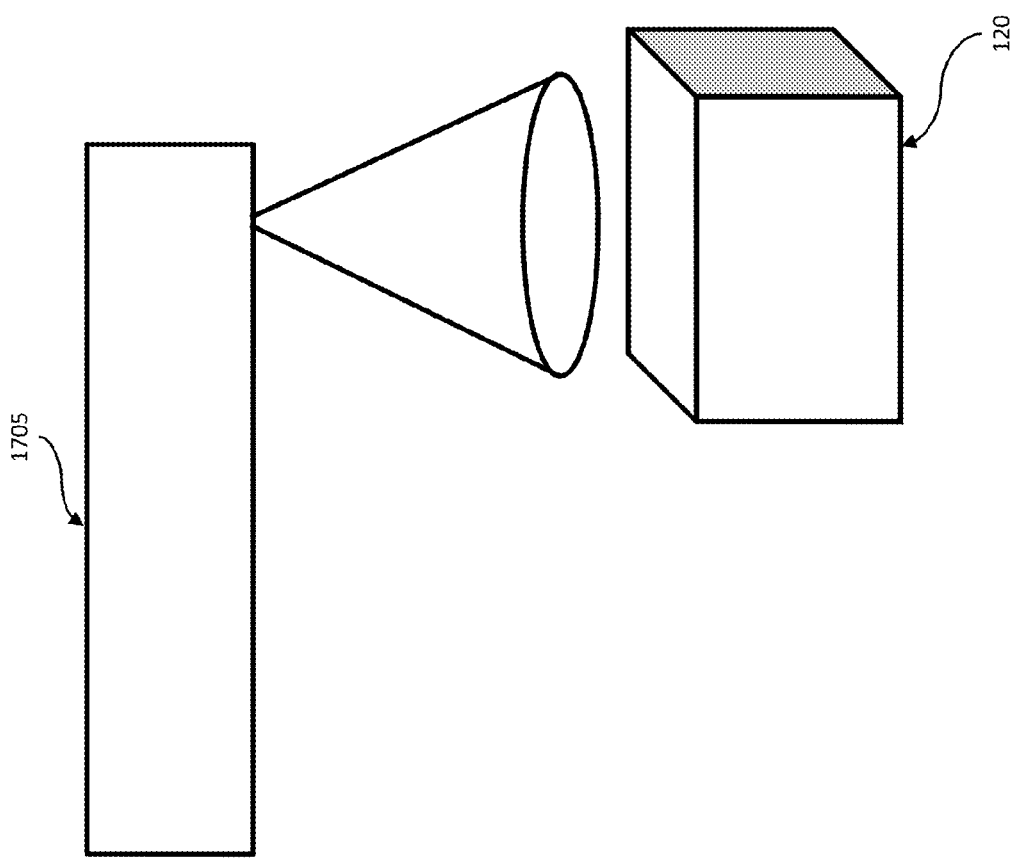
FIG. 17 is an illustration of a three-dimensional surface camera imaging an unwanted object.

However, it will often be the case where the unwanted object is fixed inside of a patient's mouth. In this case, the unwanted object may not be readily removable and scannable separately from the patient's mouth. In such a case, in one example, a three-dimensional surface camera 1705 (FIG. 17), such as the CEREC system developed by Sirona, can be used to scan the unwanted object 120 and generate three-dimensional surface data thereof. From the three-dimensional surface data of the unwanted object 120, and knowledge of the attenuation coefficient of the material, volumetric data of the unwanted object 120 can be generated. For example, the volume of an unwanted object 120 may be assigned a constant attenuation value thus treating the unwanted object 120 as a homogenous material.

If the unwanted object 120 is treated as a non-homogenous material, then respective attenuations coefficients may be assigned to the voxels of the unwanted object 120. The surface color of the object may be used as a guide to assign different attenuation coefficients. Metallic objects, which tend to have higher attenuation coefficients, are typically darker colored objects (i.e., closer to black than white in the spectral range). Accordingly, darker colored objects may be assigned a high attenuation coefficient than lighter colored objects. The attenuation coefficients may be scaled to the spectral range. Thus, a maximum attenuation coefficient may correspond to an RGB value of (0, 0, 0), i.e., pure black, and a minimum attenuation coefficient may correspond to an RGB value of (255, 255, 255). Of course, these values are merely exemplary. The relationship between attenuation coefficient and RGB value may be expressed as a function, $\mu_{RGB}=f(R,G,B)$, where f(R,G,B) is supplied by a user based on known relationships between surface color and attenuation coefficients. The gradient of f(R, G, B) may exhibit linear or non-linear characteristics. Thus, not only may attenuation coefficients vary depending on lightness versus darkness, but also based on color, i.e., red versus blue versus green.

Once an attenuation coefficient is assigned based on surface color, that coefficient may be assigned to voxels beneath the surface. In one embodiment, the attenuation coefficient of a surface voxel may be assigned to voxels below the surface to a certain depth. Thus, if it is known that a different material is located a certain depth below the surface, that depth may be a delineation point. In another embodiment, the attenuation coefficient of the surface voxel may be diffused through object in the depth direction.

Of course, the 3D surface data may also be obtained through other means as well. For example, a CAD drawing or some other electronic model of the unwanted object 120 may be available along with the information on the material and its attenuation properties. From this information, the volumetric data of the unwanted object 120 may be created. For example, a stored library of models of different dental implants, along with information about what the implant is made of, can be provided in a database. Such information can include the attenuation coefficients of the materials used, or such attenuation coefficients can be determined based on the identified materials.

Figure 18:
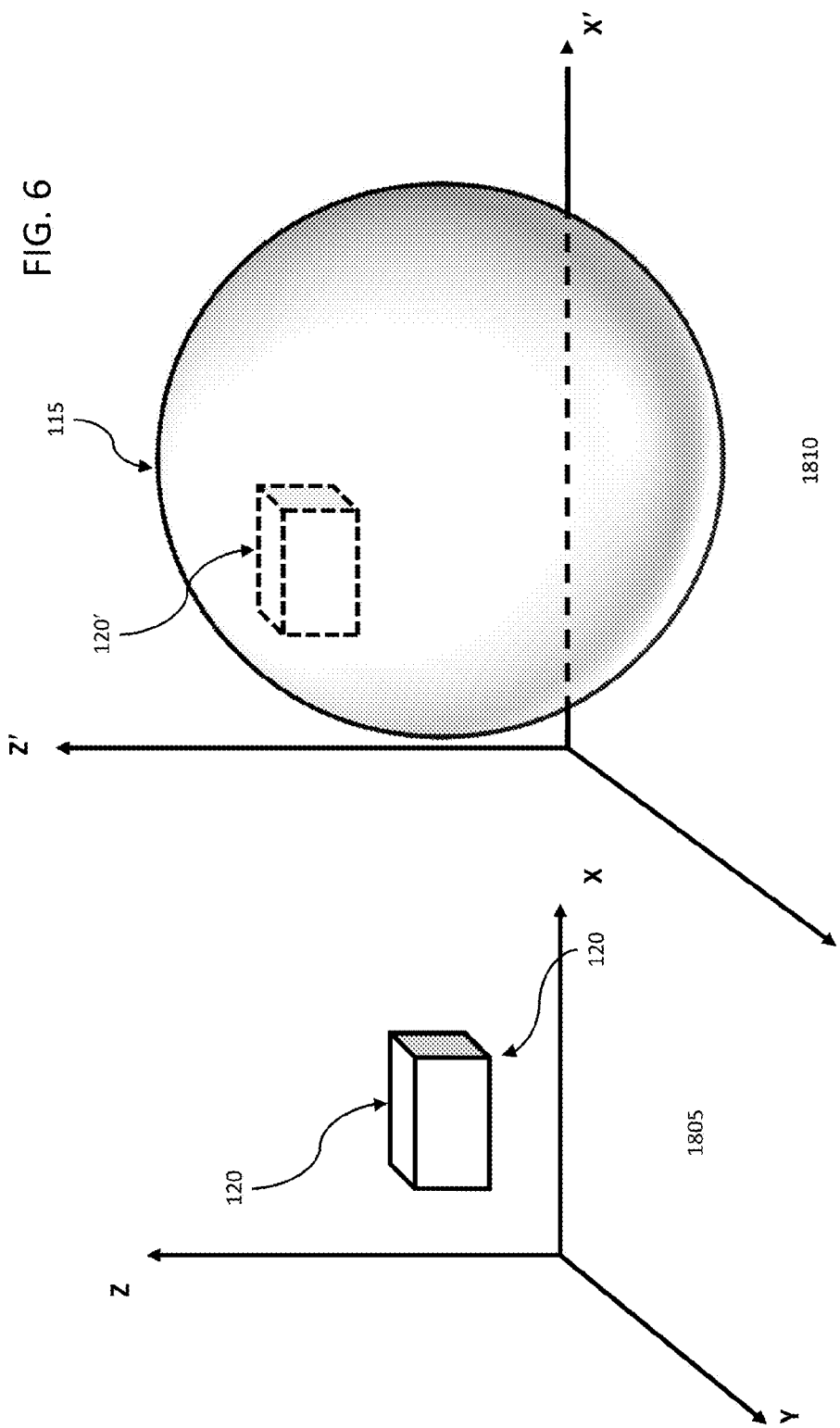
FIG. 18A is an illustration of an unwanted object in a first coordinate system.
FIG. 18B is an illustration of an object of study in a second coordinate system.

Referring now to step S215, once the volumetric data of the unwanted object 120 is obtained, it is registered with the volumetric data of the object of study 115, with the unwanted object 120 contained therein (S215). Registration is a process of aligning two or more sets of volumetric data within a common coordinate system, such that the same points in space overlap with each other as near as possible. FIGS. 18A and 18B are illustrative of two 3D images corresponding to respective sets of volumetric data. The first 3D image (1805) shows the unwanted object 120 in a first coordinate system (X, Y, Z). The second 3D image (1810) shows the object of study 115, with the unwanted object 120' contained therein, in a second coordinate system (X', Y', Z'). Here unwanted objects 120 and 120' are the same object but located at different coordinates within their respective coordinate systems. By registering the two sets of volumetric data, the unwanted objects 120 and 120' will have the same or substantially the same spatial coordinates in the common coordinate system.

Figure 19:
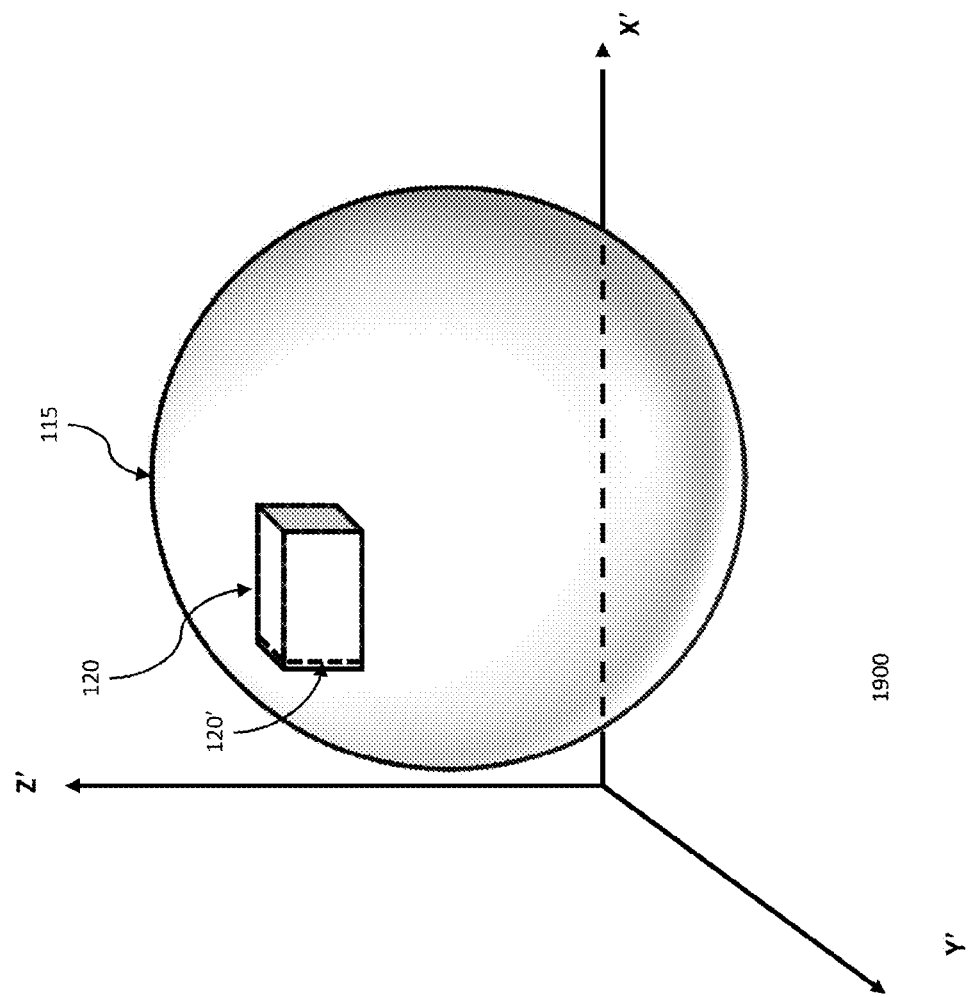
FIG. 19 is an illustration of registered volumetric data sets in a common coordinate system.

One exemplary method for registering the two sets of volumetric data is to fix the spatial coordinates of one set of volumetric data and perform a series of spatial translations of the other set of volumetric data, each time comparing a difference between the two sets of volumetric data to determine whether the sets are aligned. After each translation, the volumetric data in one set is subtracted from the other to obtain a difference. This difference is compared to a previous difference to determine whether the spatial translation brought the two sets of data into closer alignment. If the two data sets are not sufficiently aligned, another spatial translation is computed from a comparison of the previous differences. This method is one preferred method for this application, because one of the sets volumetric data likely includes only the unwanted object. As such, when the two sets of volumetric data are aligned, the spatial positions of the unwanted objects 120 and 120' will be aligned, and thus a difference between the two volumetric data sets will be an absolute minimum. Any further translation of one of the volumetric data sets will result in an increase in the computed difference away from the absolute minimum. FIG. 19 shows the result of the registration process, with the volumetric data sets aligned at the same positional coordinates in the second coordinate system 1900 (X', Y', Z'). Of course, both volumetric data sets may also be translated to achieve registration in a common coordinate system (X", Y", Z"). Once the volumetric data sets are co-registered it is possible to segment the unwanted object 120 (S220).

Segmentation is the process of partitioning the volumetric data into a plurality of segments, i.e., groups of data. Each element within the volumetric data is assigned to a segment. Boundaries between segments may be determined based on differences between attenuation coefficients of neighboring voxels. In addition, boundaries between segments in the volumetric data of the unwanted object 120 may be used to determine boundaries between segments in the volumetric data of the object of study 115. Since the volumetric data of the unwanted object 120 and the volumetric data of the object of study 115 have been coregistered within a common coordinate system, the boundaries between segments in the volumetric data of the unwanted object 120 may be used to determine corresponding boundaries between segments in the volumetric data of the object of study 115. Once the unwanted object 120 is segmented within the volumetric of data of the object of study 115, it may be removed and, if desired, replaced within interpolated data.

Figure 20:
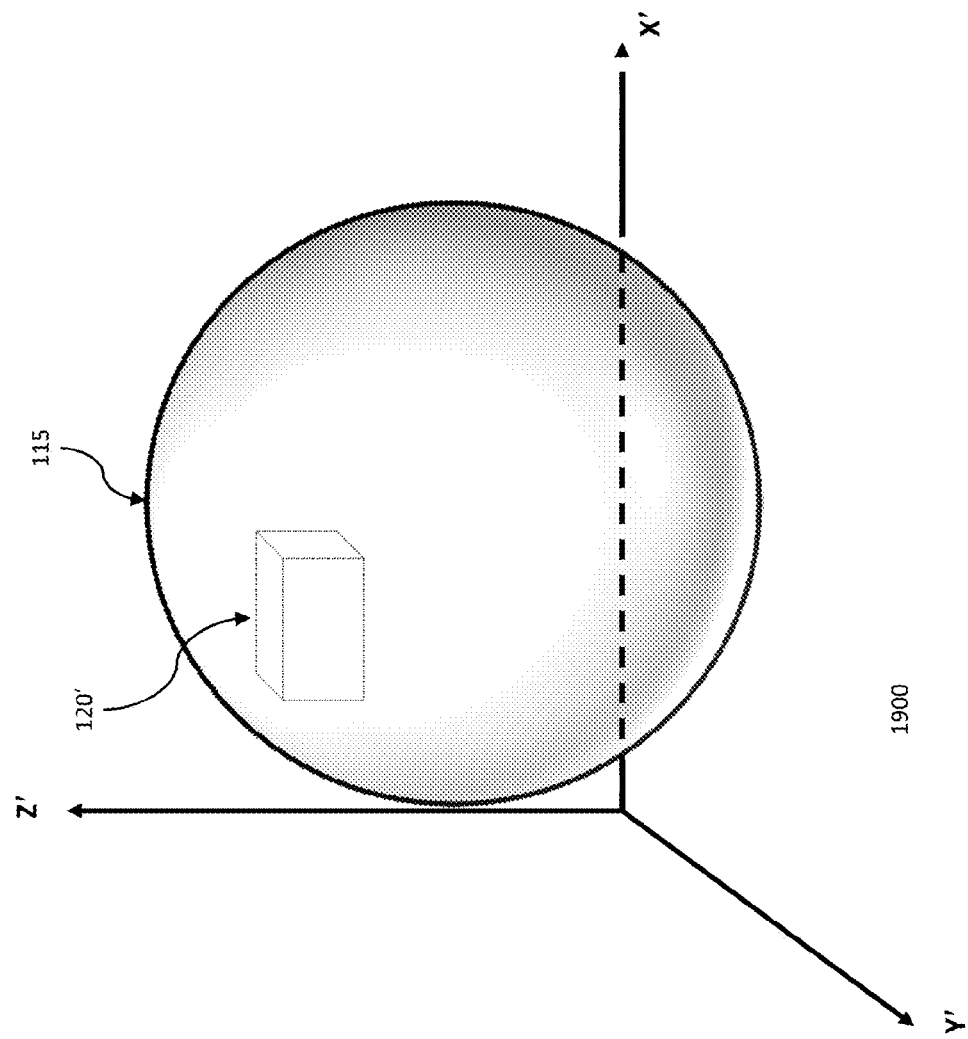
FIG. 20 is an illustration of a volumetric data set in a common coordinate system with an unwanted object removed.

FIG. 20 illustrates one method for removing the unwanted object 120 from the volumetric data of object of study 115. In FIG. 20 the dashed line indicates that the volumetric data corresponding to unwanted object 120' has been subtracted from the volumetric data of the object of study 115 (which included the unwanted object 120'). While this method of removing the object is the quickest to perform, it may not remove the negative effects of the unwanted object 120' because the removal is performed on volumetric data, which may include artifacts created from the reconstruction process used to generate the volumetric data. Therefore, in one embodiment, it may be preferable to perform a series of forward projections (as discussed below in regard to step S230) on the modified volumetric data (that is with the unwanted object removed) to create a plurality of planar projections from which a tomogram can be constructed that eliminates both the unwanted object 120 and its negative effects.

Figure 21:
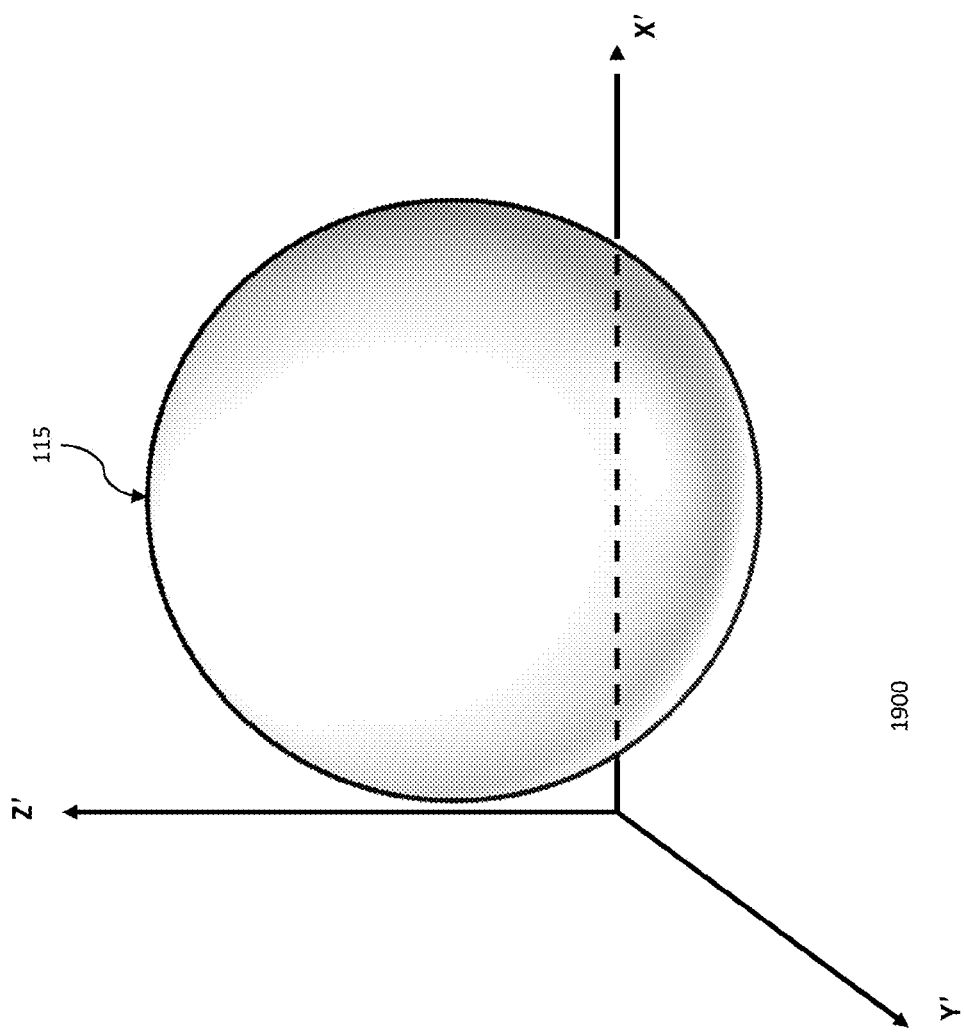
FIG. 21 is an illustration of a volumetric data set in a common coordinate system with an unwanted object removed and the corresponding voxels populated with interpolated data.

However, completely removing the unwanted object 120 from the volumetric data of the object of study 115 may be undesirable. Therefore, in another embodiment, voxels within the image volume corresponding to the removed object may be filled with data interpolated from the surrounding image volume. In the case illustrated in FIG. 21, this would result in a homogenous representation. Whether to perform interpolation or not may depend on the type of unwanted object 120 (e.g., a bite-block versus a dental restoration), the attenuation properties of the unwanted object 120, and its location.

The interpolation process (S225) will be described below with respect to the two-dimensional model described above and illustrated in FIGS. 3-9. FIG. 22A shows an image constructed from volumetric data of the object of study 115 that includes the unwanted object 120 (the four darker pixels located near the center, corresponding to $Y_1$, $Y_2$, $Y_3$, and $Y_4$ in FIG. 22E). FIG. 22B shows the corresponding absorption values from the volumetric data. FIG. 22C is an image of the same region illustrated in FIG. 22A, with the unwanted object 120 removed by the process described above. As shown in FIG. 22D, the pixels corresponding to the unwanted object now carry an absorption value of 0 (as compared to 25 previously), which means that no attenuation of the beam occurs in this region.

FIG. 22E illustrates the four pixels ($Y_1$, $Y_2$, $Y_3$, and $Y_4$) corresponding to region where the removed unwanted object 120 was located. Pixels $X_{ij}$ are pixels surrounding the region where the removed unwanted object 120 was located. One method for generating data for pixels $Y_1$, $Y_2$, $Y_3$, and $Y_4$ is to interpolate data from pixels X. Various interpolation techniques may be used depending on the degree of accuracy sought versus computational time. For example, one technique would be to assign pixels $Y_1$, $Y_2$, $Y_3$, and $Y_4$ an average value from four surrounding pixels. FIG. 22F shows respective equations for obtaining values for pixels $Y_1$, $Y_2$, $Y_3$, and $Y_4$ from pixels located above, below, left, and right of the target pixel. The equations shown in FIG. 22F are dependent equations, which can be solved simultaneously through an iterative process by assigning each of pixels $Y_1$, $Y_2$, $Y_3$, and $Y_4$ an initial condition and then waiting for a solution converge. In this case, if the initial values are the absorption values shown in FIG. 22D, the solution will converge to a homogenous distribution, as illustrated in FIG. 22G.

Of course, this is only one type of interpolative technique that may be applied. Numerous other techniques could also be applied. For example, pixels $Y_1$, $Y_2$, $Y_3$, and $Y_4$ may also be populated based on data included from diagonally adjacent pixels (such as $X_{11}$, $X_{13}$, $X_{31}$, and $Y_4$ for pixel $Y_1$). The diagonally adjacent pixels may be weighted equally or given less weight. Still further, data from pixels located farther away from the target pixel may also be used and may be weighted to give less influence compared to pixels located closer to the target pixel. The appropriate weighting of distant pixels (or voxels) may be determined by non-linear techniques, which place a greater emphasis on pixels (voxels) located closer to a target pixel. Different interpolation techniques such as bilinear, multilinear, multipolynomial, or nearest-neighbor techniques may also be used to populate the pixels/voxels.

The system illustrated in FIGS. 22A-22G is a two-dimensional representation. However, this technique can be applied to three dimensions. In three dimensions, the removal of the unwanted object 120 from the volumetric data creates a plurality of empty voxels. Like in the two-dimensional representation, those voxels may be filled with data from surrounding voxels. For instance, data for a given voxel may be interpolated from voxels immediately surrounding the given voxel, as well as data from other voxels with or without an appropriate weighting value.

Once pixels (or voxels in the three-dimensional case) are populated with interpolated data (or not as the case may be), a series of forward projections are made through the modified volumetric data of the object of study 115 in step S230. As discussed above, the volumetric data is a three-dimensional array with each element in the array containing a data value representing an amount of beam attenuation for a corresponding voxel. In a forward projection, the attenuation data is used to simulate the passage of a beam of radiation through the image volume. The result of the forward projection is a simulated two dimensional planar projection image, also referred to as a virtual exposure. By performing a plurality of forward projections through the modified volumetric data at angles ranging from 0°-180°), a corresponding series of planar projection images of the modified image volume (i.e., with the unwanted object removed or replaced by interpolated data) are produced.

Figure 23:
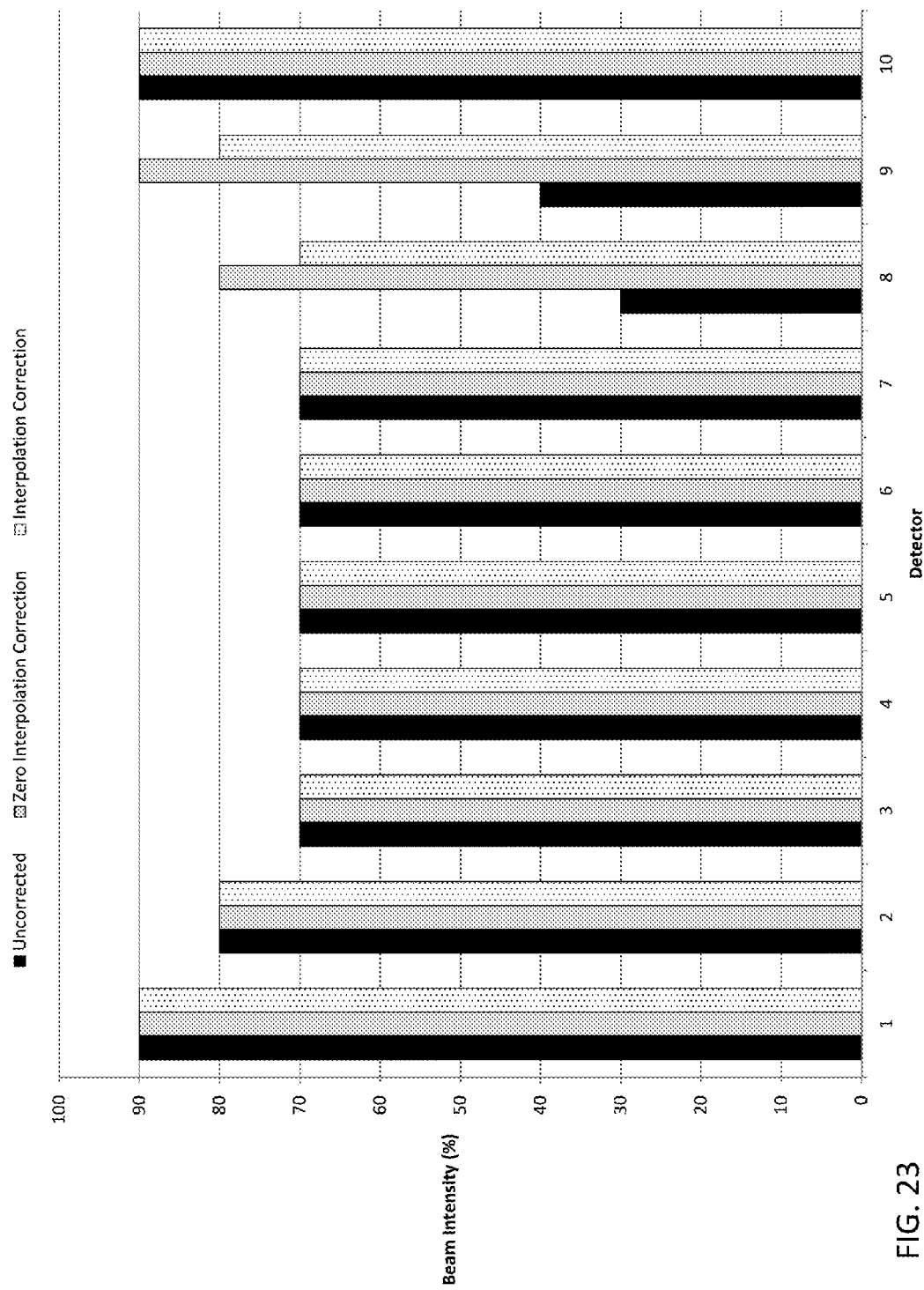
FIG. 23 is a graph of beam intensity for respective detector elements when the imaging apparatus is at the first position compared with beam intensities calculated during a forward projection at the same position through two volumetric data sets.
Figure 24:
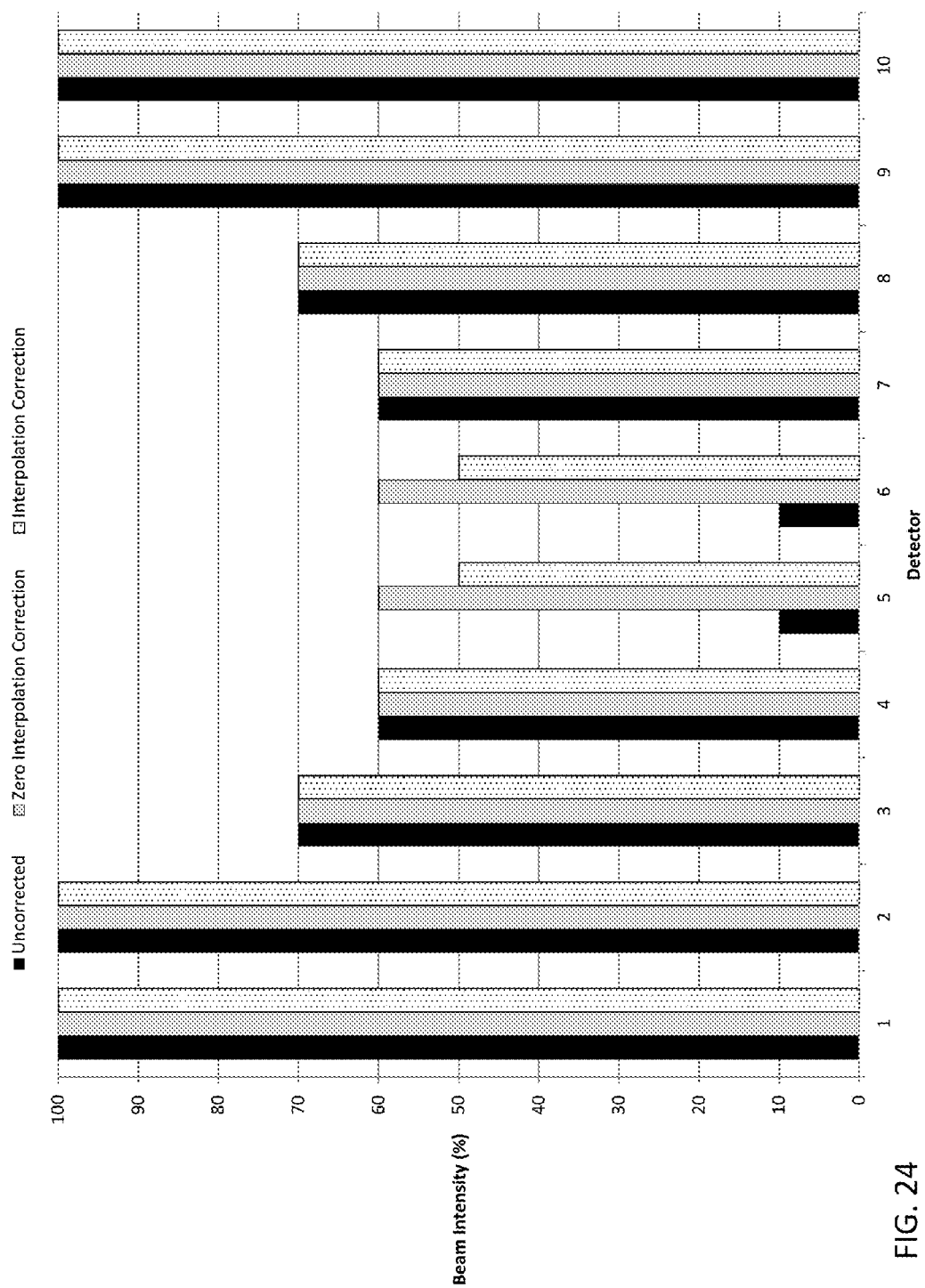
FIG. 24 is a graph of beam intensity for respective detector elements when the imaging apparatus is at the second position compared with beam intensities calculated during a forward projection at the same position through two volumetric data sets.
Figure 25:
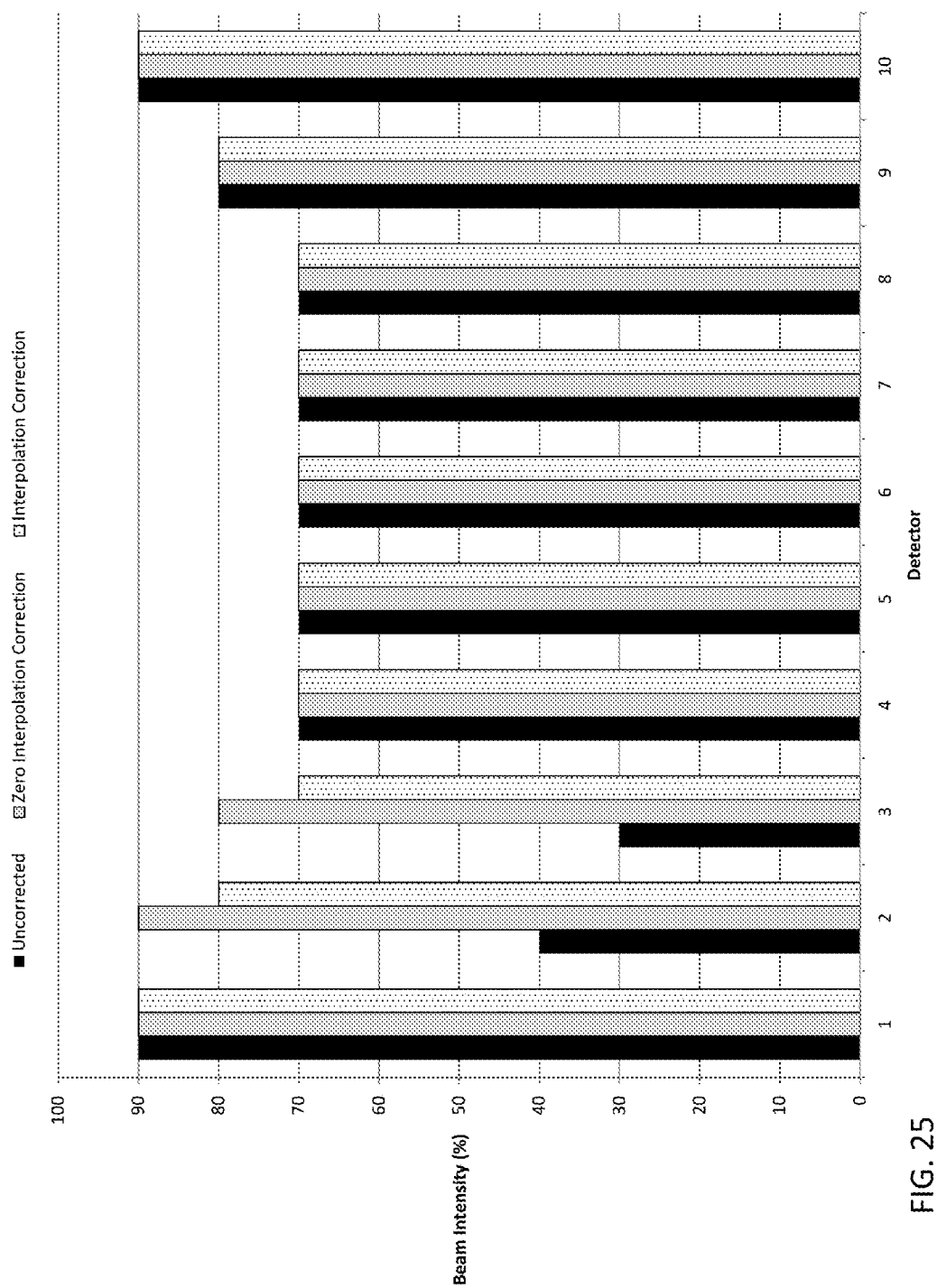
FIG. 25 is a graph of beam intensity for respective detector elements when the imaging apparatus is at the third position compared with beam intensities calculated during a forward projection at the same position through two volumetric data sets.

FIGS. 23-25 are illustrative of the difference between the actual recorded beam intensities from exposures at 0°, 90°, and 180° (represented by black bars), and the virtual exposures at the same angles where (i) the unwanted object 120 was removed without performing any interpolation (represented by gray bars) and (ii) the unwanted object 120 was removed and interpolation was subsequently performed (represented by hashed bars). In the case where the unwanted object 120 was removed without performing any subsequent interpolation, the recorded intensities from the forward projections are higher than in a case where interpolation was performed. This is because the area (or volume in three dimensions) corresponding to the unwanted object is considered empty space and thus does not contribute to beam attenuation. However, in the case where the pixels (voxels) are filled with interpolated data, the recorded intensities are reduced proportionally. From the plurality of forward projections, respective sinograms of the modified image volume may be produced, as shown in FIGS. 26A and 26B. FIG. 26A is a sinogram corresponding to a case where the volume corresponding to the unwanted object was filled with interpolated data, and FIG. 26B is sinogram corresponding to a case where the volume was not filled with interpolated data. With the sinogram of the modified image volume obtained, it is now possible to create a tomogram of the modified image volume (S235).

One of the advantages of the above-described method is that because two volumetric data sets are registered in a common coordinate system, the unwanted object 120 can be precisely located in the volumetric data of the object of interest 115. By precisely locating the unwanted object 120 within the volumetric data of the object of interest 115, the unwanted object 120 can be removed and that portion of the image volume populated with data from the surrounding volume, if desired.

Figure 27C:
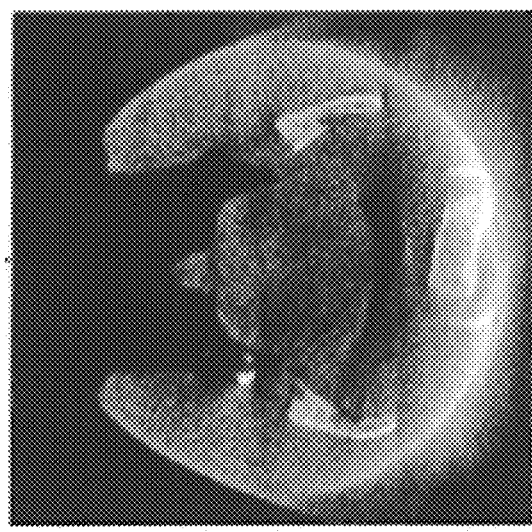
FIGS. 27A-27C are tomograms of an original scan, a scan of an objected to be removed, and a corrected original scan.
Figure 27B:
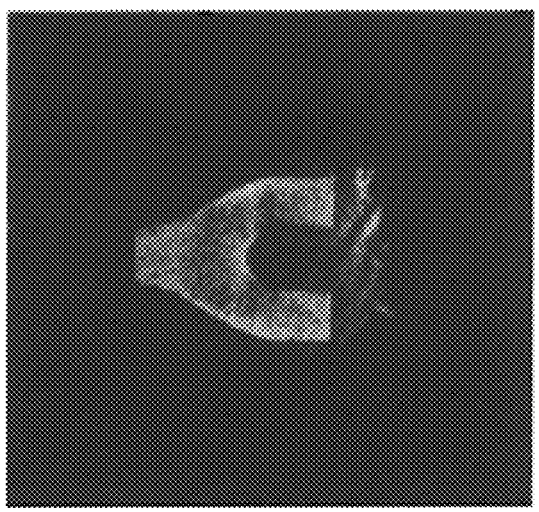
Figure 27A:
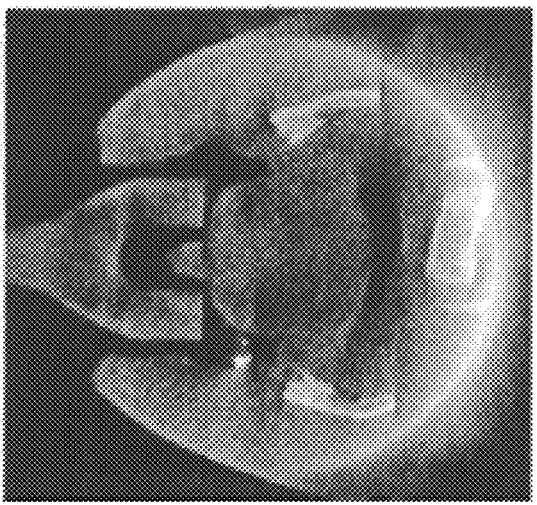

FIGS. 27A-27C are illustrative of using the above-described techniques to remove an unwanted object with an attenuation coefficient ($\mu$) that is substantially similar to the attenuation coefficient ($\mu$) of the surrounding material. FIG. 27A is a tomographic image of an object of study with an unwanted object (a bite-block) 2705 therein. The bite-block 2705 is made of a plastic material with an attenuation coefficient ($\mu$) that is substantially similar to the surrounding soft tissue. FIG. 27B is a tomographic image of the bite-block 2705 itself obtained in a separate scan. Employing steps S215, S220, S230, and S235 discussed above, the two sets of volumetric data corresponding to FIGS. 27A and 27B are registered in a common coordinate system, after which the unwanted object 2705 is segmented and removed from the volumetric data of the object of study. Forward projections are then performed on the modified volumetric data, followed by construction of a tomogram with the unwanted object removed, as shown in FIG. 27C. Since the forward projections are performed on modified volumetric data (with the unwanted objected removed), the resulting two-dimensional planar projection images will not reflect the unwanted object's 2705 presence or include artifacts (or noise) generated by the unwanted object 2705. Thus, the reconstruction algorithm will not mistakenly interpret those artifacts or noise as features, thus producing a better tomogram.

Figure 28B:
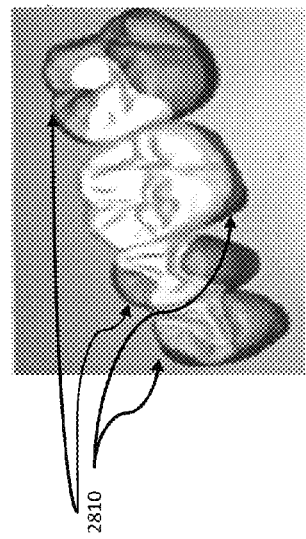
FIGS. 28A-28D are illustrations showing the process of removing a dental restoration from an object of study.
Figure 28D:
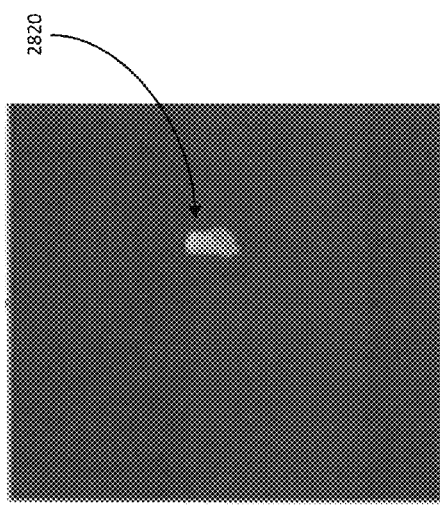
Figure 28A:
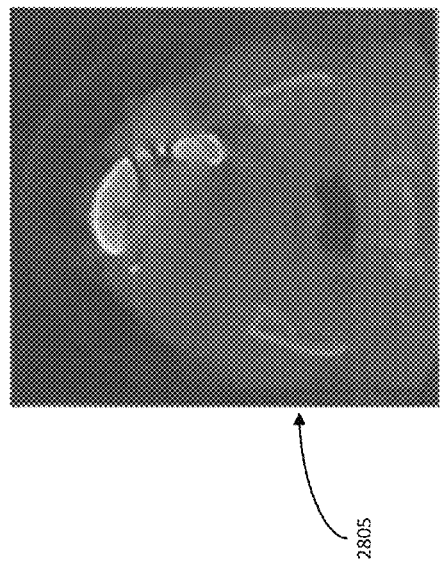
Figure 28C:
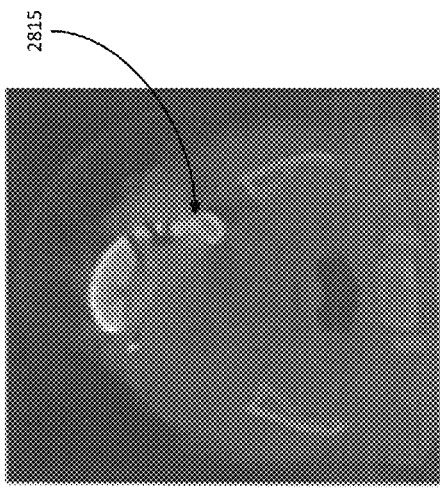

FIGS. 28A-D are illustrative of segmenting and removing a dental restoration affixed inside of a patient mouth. FIG. 28A is a tomogram of an object of study 2805. The object of study 2805 includes a plurality of dental restorations 2810 illustrated in FIG. 28B. FIG. 28B is a three-dimensional image obtained from three-dimensional surface scan data of the restoration using the three-dimensional surface camera described above and illustrated in FIG. 17. FIG. 28C illustrates the location of the restoration 2815 in the tomogram of the object of study 2805. FIG. 28D is a tomogram representing volumetric data calculated from the three-dimensional surface scan data of the dental restoration and the information regarding the attenuation coefficient of the material comprising the dental restoration. With volumetric data sets of the object of study 2805 and the dental restoration 2820, it is possible to use the above-described techniques to remove the dental restoration from the tomogram of the object of study 2805. This may allow for underlying features of interest (e.g., a cavity developing underneath the dental restoration) which were obscured from view by the dental restoration to be revealed in a tomogram generated by forward projections through the modified volumetric data (with the dental restoration removed).

Another advantage of this technique is that objects for positioning the patient but which may cause artifacts or noise can be used and then later removed through techniques described above. More specifically, volumetric data of the positional aids can be obtained by one of the methods described above. After the object of study is scanned to create corresponding volumetric data, the two sets of volumetric data can be registered in a common coordinate system. The positional aids are then segmented, and may (or may not) be removed from the volumetric data of the object of study by the techniques discussed above. The benefit of this approach is that movement artifacts caused by motion of the patient may be reduced by using the positional aids—without the positional aids themselves negatively affecting the tomographic image.

In a typical CBCT system, processing of the data generated during the CBCT scan is performed by the CBCT system itself through execution of a control program stored in memory by a CPU. The steps illustrated in the figures and described above may be implemented by a computer specifically configured to process the volumetric data according to above-described method. In one embodiment, however, such data processing may be performed by a remote computer as well. The resulting tomogram constructed from the plurality of planar projections created from a corresponding number of forward projections of the modified volumetric data of the object of study 115, may be displayed on a display unit of the CBCT system.

While various example embodiments of the invention have been described above, it should be understood that they have been presented by way of example, and not limitation. It is apparent to persons skilled in the relevant art(s) that various changes in form and detail can be made therein. Thus, the disclosure should not be limited by any of the above described example embodiments, but should be defined only in accordance with the following claims and their equivalents.

In addition, it should be understood that the figures are presented for example purposes only. The architecture of the example embodiments presented herein is sufficiently flexible and configurable, such that it may be utilized and navigated in ways other than that shown in the accompanying figures.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

What is claimed is:
1. A method, comprising:
registering first volumetric data, corresponding to an image volume comprising an object of study and an unwanted object, and second volumetric data, corresponding to the unwanted object, in a common coordinate system;
removing the unwanted object from the first volumetric data to generate modified first volumetric data;

performing a plurality of forward projections on the modified first volumetric data to generate a plurality of planar projection images;

constructing a three-dimensional image of the image volume from the plurality of planar projection images, wherein the three-dimensional image does not contain the unwanted object.

2. The method of claim 1, further comprising:
populating voxels in the modified first volumetric data corresponding to a position of the removed unwanted object with interpolated data.

3. The method of claim 1, wherein an attenuation coefficient of the unwanted object is substantially similar to an attenuation coefficient of a material adjacent to the unwanted object.

4. The method of claim 1, wherein the second volumetric data corresponding to the unwanted object is derived from three-dimensional surface scan data of the unwanted object and an attenuation coefficient of a material comprising the unwanted object.

5. The method of claim 1, further comprising:
generating the second volumetric data corresponding to the unwanted object from a radiographic scan of the unwanted object.

6. The method of claim 1, wherein the second volumetric data is derived from a three-dimensional model of the unwanted object and an attenuation coefficient of a material comprising the unwanted object.

7. The method of claim 1, further comprising:
displaying the three-dimensional image of the image volume, without the unwanted object, on a display unit.

8. A apparatus, comprising:
a processor; and
a memory storing a control program, wherein the processor and the memory are configured to:
(i) register first volumetric data, corresponding to an image volume comprising an object of study and an unwanted object, and second volumetric data, corresponding to the unwanted object, in a common coordinate system;
(ii) remove the unwanted object from the first volumetric data to generate modified first volumetric data;
(iii) perform a plurality of forward projections on the modified first volumetric data to generate a plurality of planar projection images; and
(iv) construct a three-dimensional image of the image volume from the plurality of planar projection images, wherein the three-dimensional image does not contain the unwanted object.

9. The apparatus of claim 8, wherein the processor and the memory are further configured to populate voxels in the modified first volumetric data corresponding to a position of the removed unwanted object with interpolated data.

10. The apparatus of claim 8, wherein an attenuation coefficient of the unwanted object is substantially similar to an attenuation coefficient of a material adjacent to the unwanted object.

11. The apparatus of claim 8, wherein the second volumetric data corresponding to the unwanted object is derived from three-dimensional surface scan data of the unwanted object and an attenuation coefficient of a material comprising the unwanted object.

12. The apparatus of claim 8, wherein the second volumetric data corresponding to the unwanted object is generated from a radiographic scan of the unwanted object.

13. The apparatus of claim 8, wherein the second volumetric data is derived from a three-dimensional model of the unwanted object and an attenuation coefficient of a material comprising the unwanted object.

14. The apparatus of claim 8, further comprising:
a display unit configured to display the three-dimensional image of the image volume, without the unwanted object.

15. A non-transitory computer readable storage medium storing a computer program for causing a computer to execute a method comprising:
registering first volumetric data, corresponding to an image volume comprising an object of study and an unwanted object, and second volumetric data, corresponding to the unwanted object, in a common coordinate system;
removing the unwanted object from the first volumetric data to generate modified first volumetric data;
performing a plurality of forward projections on the modified first volumetric data to generate a plurality of planar projection images;
constructing a three-dimensional image of the image volume from the plurality of planar projection images, wherein the three-dimensional image does not contain the unwanted object.

16. The non-transitory computer readable storage medium according to claim 15, wherein the method further comprises:
populating voxels in the modified first volumetric data corresponding to a position of the removed unwanted object with interpolated data.

17. The non-transitory computer readable storage medium according to claim 15, wherein an attenuation coefficient of the unwanted object is substantially similar to an attenuation coefficient of a material adjacent to the unwanted object.

18. The non-transitory computer readable storage medium according to claim 15, wherein the second volumetric data corresponding to the unwanted object is derived from three-dimensional surface scan data of the unwanted object and an attenuation coefficient of a material comprising the unwanted object.

19. The non-transitory computer readable storage medium according to claim 15, wherein the second volumetric data corresponding to the unwanted object is generated from a radiographic scan of the unwanted object.

20. The non-transitory computer readable storage medium according to claim 15, wherein the second volumetric data is derived from a three-dimensional model of the unwanted object and an attenuation coefficient of a material comprising the unwanted object.

* * * * *